(12) United States Patent
Simmons et al.

(10) Patent No.: US 11,795,435 B2
(45) Date of Patent: Oct. 24, 2023

(54) POTENCY ASSAY

(71) Applicant: Mesoblast International Sàrl, Meyrin (CH)

(72) Inventors: Paul Simmons, Malbourne (AU); Colby Suire, New York, NY (US); Fiona See, New York, NY (US)

(73) Assignee: MESOBLAST INTERNATIONAL SÁRL;, Meyrin (CH)

( * ) Notice: Subject to any disclaimer, the term of this patent is extended or adjusted under 35 U.S.C. 154(b) by 1185 days.

(21) Appl. No.: 15/571,178

(22) PCT Filed: May 4, 2016

(86) PCT No.: PCT/EP2016/060049
§ 371 (c)(1),
(2) Date: Apr. 29, 2019

(87) PCT Pub. No.: WO2016/177805
PCT Pub. Date: Nov. 10, 2016

(65) Prior Publication Data
US 2020/0140822 A1    May 7, 2020

(30) Foreign Application Priority Data
May 5, 2015 (AU) .............................. 2015901605

(51) Int. Cl.
*C12N 5/0775* (2010.01)
*G01N 33/68* (2006.01)
(Continued)

(52) U.S. Cl.
CPC ............ *C12N 5/0663* (2013.01); *A61K 35/28* (2013.01); *A61K 47/36* (2013.01);
(Continued)

(58) Field of Classification Search
CPC .............. C12N 5/0663; C12N 2500/30; C12N 2501/15; A61K 35/28; A61K 47/36; G01N 33/6863; G01N 2333/495; G01N 2800/10
See application file for complete search history.

(56) References Cited

FOREIGN PATENT DOCUMENTS

| JP | 2011-196840 A | 10/2011 |
|---|---|---|
| KR | 10 2007 0018738 | 2/2007 |
| KR | 10 2015 0016117 | 2/2015 |

OTHER PUBLICATIONS

Cao et al. "Bone marrow mesenchymal stem cells slow intervertebral disc degeneration through the NF-KB pathway" The Spine Journal 15 (2015); 530-538. (Year: 2015).*

(Continued)

*Primary Examiner* — Marcia S Noble
*Assistant Examiner* — Lauren K Van Buren
(74) *Attorney, Agent, or Firm* — John P. White

(57) ABSTRACT

The present invention relates to a method for determining the biological activity or therapeutic efficacy of cultured mesenchymal lineage precursor cells or stem cells based on their released TGF-9 levels in culture. The present invention also relates to isolated populations of mesenchymal lineage precursor cells or stem cells selected based on the level of TGF-9 levels released by such cells in culture. The present invention further relates to treatment of a subject suffering from a degenerative disc disease by administering such selected cell populations.

11 Claims, 15 Drawing Sheets

(51) Int. Cl.
A61K 35/28 (2015.01)
A61K 47/36 (2006.01)
(52) U.S. Cl.
CPC ..... *G01N 33/6863* (2013.01); *C12N 2500/30* (2013.01); *G01N 2333/495* (2013.01)

(56) References Cited

OTHER PUBLICATIONS

Cao et al. "Bone marrow mesenchymal stem cells slowly intervertebral disc degeneration through the NF-KB pathway" The Spine Journal (2015) 530-538 (Year: 2015).*

Jurukovski "Methods for Measuring TGF-beta Using Antibodies, Cells, and Mice" Methods in Molecular Medicine 117: 161-75 (Year: 2005).*

English Translation of Mar. 23, 2020 Office Action in connection with Japanese Patent Application No. 2017-557438.

Akira Kinoshita et al. "Bone and cartilage disease caused by TGF signaling disorder—from monogenic diseases to common diseases", Journal of Clinical and Experimental Medicine, 2010, vol. 234, No. 10, pp. 987-992.

Cao et al., "Bone marrow mesenchymal stem cell intervertebral disc degeneration through the NF-Kb pathway", The Spine Journal, 2015, vol. 15, 530-538, Basic Science.

International Search Report dated Aug. 3, 2016 in connection with PCT International Application No. PCT/EP2016/060049.

Written Opinion of the International Searching Authority dated Aug. 3, 2016 in connection with PCT International Application No. PCT/EP2016/060049.

Cheng Cao, et al., "Bone marrow mesenchymal stem cells slow intervertebral disc degeneration through the NF-kB pathway", The Spine Journal, Mar. 1, 2015, vol. 15, No. 3, pp. 530-538.

Li Wen, et al., "Immunomodulatory Effects of Bone Marrow-Derived Mesenchymal Stem Cells on Pro-Inflammatory Cytokine-Stimulated Human Corneal Epithelial Cells", PLOS ONE, Jul. 8, 2014, vol. 9, No. 7, el01841.

Dobroslav Kyurkchiev, et al., "Secretion of immunoregulatory cytokines by mesenchymal stem cells", World Journal of Stem Cells, Jan. 1, 2014, vol. 6, No. 5, pp. 552-570.

* cited by examiner

A 25,000 cells/cm²

B 50,000 cells/cm²

A

Standard curve in Calibrator diluent -1

Standard curve in Calibrator diluent -2

Standard curve in Calibrator diluent -3

B

Standard curve in CBM +0.5% BSA-1

Standard curve in CBM +0.5% BSA-2

Standard curve in CBM +0.5% BSA-3

POTENCY ASSAY

CROSS-REFERENCE TO RELATED APPLICATIONS

This application is a § 371 national stage of PCT International Application No. PCT/EP2016/060049, filed May 4, 2016, claiming priority of Australian Patent Application No. AU 2015901605, filed May 5, 2015, the contents of each of which are hereby incorporated by reference into the application.

TECHNICAL FIELD

BACKGROUND

Several cellular therapy products for regenerative or immune therapy applications have advanced to clinical evaluation and market authorization. However, release of these cellular therapy products onto the market is hindered by their complexity and heterogeneity, which makes identification of relevant biologic activities, and thus definition of consistent cellular therapy product quality, difficult.

Physiochemical parameters (for example, characterization of size, morphology, light-scattering properties, tensile strength, cell number, confluence, identification of phenotypic markers, secreted substances, genotype, gene expression profile) are routinely used for identification and quantification of the active substance, intermediates, impurities and contaminants. However, physiochemical parameters cannot confirm that a product will be biologically active and potent (i.e., elicit the desired effect). In contrast, biologic characterization takes into account the effect of the product on biologic systems, either modelled in vitro or in vivo in animals and ultimately in the clinic.

Pharmaceutical legislation in the United States and Europe requires that active substances whose molecular structure cannot be fully defined be evaluated for their potency before release onto the market. It is a legal requirement to evaluate the potency of each batch of a licensed cellular therapy product.

Potency testing must demonstrate the relevant biologic activity or activities of the product. It is not a requirement for potency testing to reflect all of the product's biologic functions, but it should indicate one or more relevant biologic functions. It is expected that accuracy, sensitivity, specificity and reproducibility will be established for the analytic methods used in potency testing and that they be suitably robust.

There is a need to identify the parameters that are critical to the efficacy of cellular therapy products and to control them (e.g., via potency testing) such that products of consistent quality can be manufactured.

SUMMARY

The present inventors have developed a potency assay to measure the biological activity or therapeutic efficacy of cellular therapy products comprising mesenchymal lineage precursor or mesenchymal lineage stem cells, referred to subsequently as "mesenchymal lineage precursor or stem cells."

Accordingly, the present disclosure provides a method for determining the potency of mesenchymal lineage precursor or stem cells comprising:
(i) obtaining a population comprising mesenchymal lineage precursor or stem cells;
(ii) culturing the cells in a culture medium; and
(iii) determining the amount of TGFβ1 released by the cells into the culture medium, wherein an amount of at least about 2800 pg/$10^6$ cells TGFβ1 is indicative of biological activity or therapeutic efficacy. For example, an amount of at least about at 2810 pg/$10^6$ cells TGFβ1, at least about 2820 pg/$10^6$ cells TGFβ1, at least about 2830 pg/$10^6$ cells TGFβ1, at least about 2840 pg/$10^6$ cells TGFβ1, at least about 2850 pg/$10^6$ cells TGFβ1, at least about 2860 pg/$10^6$ cells TGFβ1, at least about 2870 pg/$10^6$ cells TGFβ1, at least about 2880 pg/$10^6$ cells TGFβ1, at least about 2890 pg/$10^6$ cells TGFβ1, at least about 2900 pg/$10^6$ cells TGFβ1, at least about 2910 pg/$10^6$ cells TGFβ1, at least about 2920 pg/$10^6$ cells TGFβ1, at least about 2930 pg/$10^6$ cells TGFβ1, at least about 2940 pg/$10^6$ cells TGFβ1, at least about 2950 pg/$10^6$ cells TGFβ1, at least about 2960 pg/$10^6$ cells TGFβ1, at least about 2970 pg/$10^6$ cells TGFβ1, at least about 2980 pg/$10^6$ cells TGFβ1, at least about 2990 pg/$10^6$ cells TGFβ1, or at least about 3000 pg/$10^6$ cells TGFβ1 is indicative of biological activity or therapeutic efficacy.

The present disclosure also provides a method for determining the potency of mesenchymal lineage precursor or stem cells comprising:
(i) obtaining a population comprising mesenchymal lineage precursor or stem cells;
(ii) culturing the cells in a culture medium; and
(iii) determining the amount of TGFβ1 released by the cells into the culture medium, wherein an amount of at least about 400 pg/ml of culture medium TGFβ1 is indicative of biological activity or therapeutic efficacy. For example, an amount of at least about 405 pg/ml of culture medium TGFβ1, at least about 410 pg/ml of culture medium TGFβ1, at least about 415 pg/ml of culture medium TGFβ1, at least about 420 pg/ml of culture medium TGFβ1, at least about 425 pg/ml of culture medium TGFβ1, at least about 430 pg/ml of culture medium TGFβ1, at least about 435 pg/ml of culture medium TGFβ1, at least about 440 pg/ml of culture medium TGFβ1, at least about 445 pg/ml of culture medium TGFβ1, at least about 450 pg/ml of culture medium TGFβ1, at least about 455 pg/ml of culture medium TGFβ1, at least about 460 pg/ml of culture medium TGFβ1, at least about 465 pg/ml of culture medium TGFβ1, at least about 470 pg/ml of culture medium TGFβ1, at least about 475 pg/ml of culture medium TGFβ1, at least about 480 pg/ml of culture medium TGFβ1, at least about 485 pg/ml of culture medium TGFβ1, at least about 490 pg/ml of culture medium TGFβ1, at least about 495 pg/ml of culture medium TGFβ1, or at least about 500 pg/ml of culture is indicative of biological activity or therapeutic efficacy.

In one embodiment, the biological activity of the cells comprises the ability to stimulate collagen production in human annulus fibrous cells in vitro.

In one embodiment, therapeutic efficacy comprises therapeutic efficacy in treatment of degenerative disc disease.

In one embodiment, the method is used to determine the potency of previously culture-expanded mesenchymal lineage precursor or stem cells. In an alternate embodiment, the method is used to determine the potency of freshly isolated mesenchymal lineage precursor or stem cells.

In one embodiment, the population is enriched for mesenchymal lineage precursor or stem cells.

In one embodiment, the method further comprises enriching for mesenchymal lineage precursor or stem cells to obtain the enriched population. For example, mesenchymal lineage precursor or stem cells are enriched for by selection of STRO-1+ cells and/or Tissue Non-Specific Alkaline Phosphatase (TNAP)+ cells.

In one embodiment, the mesenchymal lineage precursor or stem cells are human mesenchymal lineage precursor or stem cells.

In one embodiment, the method comprises seeding the cells in a culture vessel at about 50,000 viable cells/cm$^2$.

In one embodiment, the method comprises culturing the cells in chondrogenic basal medium supplemented with 0.5% bovine serum albumin.

In one embodiment, the method comprises culturing adherent cells for at least 68 to 76 hours. In one embodiment, adherent cells are first obtained by culturing the population of cells overnight in, for example, chondrogenic basal medium supplemented with 0.5% bovine serum albumin, to allow them to adhere to the culture vessel.

In one embodiment, the method comprises collecting a sample of the culture medium in which the cells were cultured. In one embodiment, the collected sample comprises all of the culture medium in which the cells were cultured.

In one embodiment, the method comprises activating latent TGFβ1 in the culture medium prior to determining the amount of TGFβ1 in the culture medium.

In one embodiment, activating latent TGFβ1 comprises adding an acid, for example, 1 N HCl, to the culture medium to lower the pH of the culture medium. In one embodiment, the method comprises concentrating the culture medium sample prior to lowering the pH. In one embodiment, the method, following addition of the acid, comprises neutralising the pH of the culture medium to 7.2 to 7.6 by adding, for example, 1.2 N NaOH/0.5 M HEPES or 1N NaOH.

In one embodiment, the method comprises determining the amount of TGFβ1 in the culture medium by enzyme-linked immunosorbent assay (ELISA).

In one example, the ELISA comprises:
(i) diluting the culture medium 1:5 in a sample diluent;
(ii) adding the diluted culture medium to a well of a microplate precoated with a monoclonal antibody specific for TGFβ1;
(iii) adding sample diluent to each well of the microplate;
(iv) incubating the microplate for 2 hours at room temperature;
(v) washing the microplate;
(vi) adding TGFβ1 conjugate to the well;
(vii) incubating the microplate for 2 hours at room temperature;
(viii) washing the microplate;
(ix) adding a substrate solution to the well;
(x) incubating the microplate for 30 minutes at room temperature;
(xi) adding a stop solution to the well;
(xii) reading optical density on a microplate reader set to 450 nm with wavelength correction at 570 nm;
(xiii) determining the concentration of TGFβ1 corrected for dilution.

In one embodiment, the sample diluent is chondrogenic basal medium supplemented with 0.5% bovine serum albumin.

In one embodiment, the method further comprising:
preparing serial dilutions of a TGFβ1 standard in a sample diluent with final concentrations ranging from 31.2-2000 pg/ml;
adding the standards to the microplate before step (iii);
constructing a standard curve using a four parameter logistic curve fit; and
determining the concentration of TGFβ1 in the culture medium by reference to the standard curve.

The present disclosure also provides a method for determining the potency of mesenchymal lineage precursor cells comprising:
(i) obtaining a population of mesenchymal lineage precursor cells;
(ii) seeding the cells in a culture vessel at 50,000 viable cells/cm$^2$;
(iii) culturing the cells in chondrogenic basal medium supplemented with 0.5% bovine serum albumin;
(iv) collecting the culture medium;
(v) activating latent TGFβ1 released by the cells into the culture medium by adding 1 N HCl to reduce the pH of the culture medium;
(vi) neutralising the pH of the culture medium to 7.2 to 7.6 by adding 1.2 N NaOH/0.5 M HEPES or 1N NaOH;
(vii) diluting the culture medium 1:5 in chondrogenic basal medium supplemented with 0.5% bovine serum albumin;
(viii) adding the diluted culture medium to a well of a microplate precoated with a monoclonal antibody specific for TGFβ1;
(ix) adding sample diluent to each well of the microplate;
(x) incubating the microplate for 2 hours at room temperature;
(xi) washing the microplate;
(xii) adding TGFβ1 conjugate to the well;
(xiii) incubating the microplate for 2 hours at room temperature;
(xiv) washing the microplate;
(xv) adding a substrate solution to the well;
(xvi) incubating the microplate for 30 minutes at room temperature;
(xvii) adding a stop solution to the well;
(xviii) reading optical density on a microplate reader set to 450 nm with wavelength correction at 570 nm;
(xix) determining the concentration of TGFβ1 corrected for dilution.

In one embodiment, the method further comprises:
preparing serial dilutions of a TGFβ1 standard in chondrogenic basal medium supplemented with 0.5% bovine serum albumin with final concentrations ranging from 31.2-2000 pg/ml;
adding the standards to the microplate before step (ix);
constructing a standard curve using a four parameter logistic curve fit; and determining the concentration of TGFβ1 in the culture medium by reference to the standard curve.

The present disclosure also provides a population of cells comprising mesenchymal lineage precursor or stem cells selected for use in treatment, wherein the population of cells releases 2800 pg/10$^6$ cells TGFβ1 when assayed in a method of the disclosure.

The present disclosure also provides an isolated population of cells comprising mesenchymal lineage precursor or stem cells selected for use in treatment, wherein the population of cells releases 400 pg/ml culture medium TGFβ1 when assayed in a method of the disclosure.

The present disclosure also provides an isolated population of cells comprising mesenchymal lineage precursor or stem cells, wherein the population of cells has been selected for use in treatment by determining release of TGFβ1 under culture conditions.

In one embodiment, the isolated population of cells comprises culture-expanded mesenchymal lineage precursor or stem cells. In an alternate embodiment, the isolated population of cells comprises freshly isolated mesenchymal lineage precursor or stem cells. In one embodiment the isolated population of cells comprises mesenchymal lineage precursor or stem cells that have been assayed to determine release of TGFβ1 under culture conditions. In another embodiment, the isolated population of cells comprises mesenchymal lineage precursor or stem cells from a population that has been sampled to determine release of TGFβ1 under culture conditions (i.e., the cells in the isolated population itself have not been assayed to determine release of TGFβ1 under culture conditions).

In one embodiment, the mesenchymal lineage precursor or stem cells comprise at least 5% of the isolated cell population.

In one embodiment, also provided is a composition comprising one of the above-mentioned isolated cell populations and a cryopreservative. In one embodiment the cryopreservative in the composition is DMSO or Profreeze™. In one embodiment the composition comprises the isolated cell population in 42.5% (v/v) Profreeze™/50% αMEM (v/v)/7.5% (v/v) DMSO.

In one embodiment, provided herein is a composition comprising one of the above-mentioned isolated cell populations and hyaluronan, for example, at least about 0.5% HA or HA salt, at least about 0.6% HA or HA salt, at least about 0.7% HA or HA salt, at least about 0.8% HA or HA salt, at least about 0.9% HA or HA salt, at least about 1% HA or HA salt, at least about 1.5% HA or HA salt, at least about 2% HA or HA salt, at least about 2.5% HA or HA salt, at least about 3% HA or HA salt, at least about 3.5% HA or HA salt, at least about 4% HA or HA salt, at least about 4.5% HA or HA salt, at least about 5% HA or HA salt, at least about 6% HA or HA salt, at least about 7% HA or HA salt, at least about 8% HA or HA salt, at least about 9% HA or HA salt, or at least about 10% HA or HA salt.

The present disclosure also provides a method of treating a subject with degenerative disc disease, the method comprising administering a composition of the disclosure to the subject.

In one embodiment, a cryopreserved composition of the disclosure is thawed and mixed with hyaluronan (HA) or a HA salt, such as, for example, sodium HA prior to administration.

The present disclosure also provides a method of treating a subject with degenerative disc disease, the method comprising administering culture medium comprising at least about 400 pg/ml culture medium TGFβ1 to the subject.

DESCRIPTION OF EMBODIMENTS

General Techniques and Definitions

Figure 1:
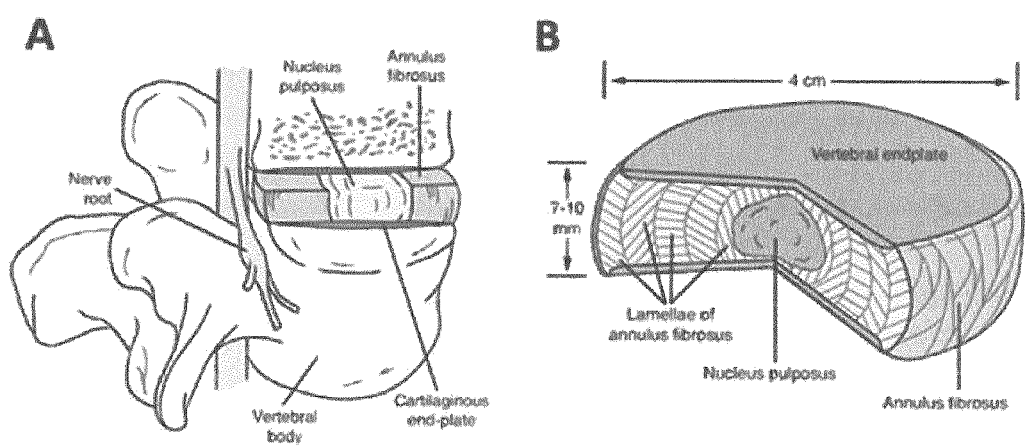
FIG. 1: Location and Structure of IVD. (A) Representation showing the location of the intervertebral disc (IVD) between 2 intervertebral bodies. (B) A view through a healthy disc showing the nucleus pulposus (NP) at the center surrounded by the annulus fibrosus (AF), and the vertebral endplate (Figure adapted from (Raj, 2008)).

Throughout this specification, unless specifically stated otherwise or the context requires otherwise, reference to a single step, composition of matter, group of steps or group of compositions of matter shall be taken to encompass one and a plurality (i.e., one or more) of those steps, compositions of matter, group of steps or group of compositions of matter.

Those skilled in the art will appreciate that the disclosure described herein is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific embodiments described herein, which are intended for the purpose of exemplification only. Functionally-equivalent products, compositions and methods are clearly within the scope of the disclosure.

Any example disclosed herein shall be taken to apply mutatis mutandis to any other example unless specifically stated otherwise.

Unless specifically defined otherwise, all technical and scientific terms used herein shall be taken to have the same meaning as commonly understood by one of ordinary skill in the art (e.g., in cell culture, molecular genetics, stem cell differentiation, immunology, immunohistochemistry, protein chemistry, and biochemistry).

Unless otherwise indicated, the stem cells, cell culture, and surgical techniques utilized in the present disclosure are standard procedures, well known to those skilled in the art. Such techniques are described and explained throughout the literature in sources such as (Perbal, 1984) (Sambrook & Green, 2012) (Brown, 1991) (Glover & Hames, 1995 and 1996) (Ausubel F. M., 1987 including all updates untill present) (Harlow & Lane, 1988) and (Coligan, Kruisbeek, Margulies, Shevach, & Strober, 1991 including all updates until present).

The term "and/or", e.g., "X and/or Y" shall be understood to mean either "X and Y" or "X or Y" and shall be taken to provide explicit support for both meanings or for either meaning.

As used herein, the term about, unless stated to the contrary, refers to +/−10%, more preferably +/−5%, of the designated value.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Mesenchymal Lineage Precursor Cells

As used herein, the term "mesenchymal lineage precursor or stem cells" refers to undifferentiated multipotent cells that have the capacity to self renew while maintaining multipotency and the capacity to differentiate into a number of cell types either of mesenchymal origin, for example, osteoblasts, chondrocytes, adipocytes, stromal cells, fibroblasts and tendons, or non-mesodermal origin, for example, hepatocytes, neural cells and epithelial cells.

The term "mesenchymal lineage precursor or stem cells" includes both parent cells and their undifferentiated progeny. The term also includes mesenchymal precursor cells, multipotent stromal cells, mesenchymal stem cells, perivascular mesenchymal precursor cells, and their undifferentiated progeny.

Mesenchymal lineage precursor or stem cells can be autologous, xenogenic, syngenic or isogenic. Autologous cells are isolated from the same individual to which they will be reimplanted. Allogeneic cells are isolated from a donor of the same species. Xenogenic cells are isolated from a donor of another species. Syngenic or isogenic cells are isolated from genetically identical organisms, such as twins, clones, or highly inbred research animal models.

Mesenchymal lineage precursor or stem cells reside primarily in the bone marrow, but have also shown to be present in diverse host tissues including, for example, cord blood and umbilical cord, adult peripheral blood, adipose tissue, trabecular bone and dental pulp.

Mesenchymal lineage precursor or stem cells can be isolated from host tissues and enriched for by selection of STRO-1+ cells. For example, a bone marrow aspirate from a subject may be further treated with an antibody to STRO-1 or TNAP to enable selection of mesenchymal lineage precursor or stem cells. In one example, the mesenchymal lineage precursor or stem cells can be enriched for by using the STRO-1 antibody described in (Simmons & Torok-Storb, 1991).

STRO-1+ cells are cells found in bone marrow, blood, dental pulp cells, adipose tissue, skin, spleen, pancreas, brain, kidney, liver, heart, retina, brain, hair follicles, intestine, lung, lymph node, thymus, bone, ligament, tendon, skeletal muscle, dermis, and periosteum; and are capable of differentiating into germ lines such as mesoderm and/or endoderm and/or ectoderm. Thus, STRO-1+ cells are capable of differentiating into a large number of cell types including, but not limited to, adipose, osseous, cartilaginous, elastic, muscular, and fibrous connective tissues. The specific lineage-commitment and differentiation pathway which these cells enter depends upon various influences from mechanical influences and/or endogenous bioactive factors, such as growth factors, cytokines, and/or local microenvironmental conditions established by host tissues. The term "enriched" as used herein describes a population of cells in which the proportion of one particular cell type or the proportion of a number of particular cell types is increased when compared with an untreated population of the cells (e.g., cells in their native environment). In one example, a population enriched for STRO-1+ cells comprises at least about 0.1% or 0.5% or 1% or 2% or 5% or 10% or 15% or 20% or 25% or 30% or 50% or 75% STRO-1+ cells. In this regard, the term "population of cells enriched for STRO-1+ cells" will be taken to provide explicit support for the term "population of cells comprising X % STRO-1+ cells", wherein X % is a percentage as recited herein. The STRO-1+ cells can, in some examples, form clonogenic colonies, for example, CFU-F (fibroblasts) or a subset thereof (e.g., 50% or 60% or 70% or 70% or 90% or 95%) can have this activity.

In one example, the population of cells is enriched from a cell preparation comprising STRO-1+ cells in a selectable form. In this regard, the term "selectable form" will be understood to mean that the cells express a marker (e.g., a cell surface marker) permitting selection of the STRO-1+ cells. The marker can be STRO-1, but need not be. For example, as described and/or exemplified herein, cells (e.g., MPCs) expressing STRO-2 and/or STRO-3 (TNAP) and/or STRO-4 and/or VCAM-1 and/or CD146 and/or 3G5 also express STRO-1 (and can be STRO-1$^{bright}$). Accordingly, an indication that cells are STRO-1+ does not mean that the cells are selected by STRO-1 expression. In one example, the cells are selected based on at least STRO-3 expression, e.g., they are STRO-3+(TNAP+).

Reference to selection of a cell or population thereof does not necessarily require selection from a specific tissue source. As described herein STRO-1+ cells can be selected from or isolated from or enriched from a large variety of sources. That said, in some examples, these terms provide support for selection from any tissue comprising STRO-1+ cells or vascularized tissue or tissue comprising pericytes (e.g., STRO-1+ pericytes) or any one or more of the tissues recited herein.

In one example, the mesenchymal lineage precursor or stem cells of the disclosure express one or more markers individually or collectively selected from the group consisting of TNAP+, VCAM-1+, THY-1+, STRO-2+, STRO-4+ (HSP-90β), CD45+, CD146+, 3G5+.

By "individually" is meant that the disclosure encompasses the recited markers or groups of markers separately, and that, notwithstanding that individual markers or groups of markers may not be separately listed herein the accompanying claims may define such marker or groups of markers separately and divisibly from each other.

By "collectively" is meant that the disclosure encompasses any number or combination of the recited markers or groups of peptides, and that, notwithstanding that such numbers or combinations of markers or groups of markers may not be specifically listed herein the accompanying claims may define such combinations or sub-combinations separately and divisibly from any other combination of markers or groups of markers.

In one example, the STRO-1+ cells are STRO-1$^{bright}$ (syn. STRO-1$^{bri}$). In one example, the STRO-1$^{bri}$ cells are preferentially enriched relative to STRO-1$^{dim}$ or STRO-1$^{intermediate}$ cells.

In one example, the STRO-1$^{bright}$ cells are additionally one or more of TNAP+, VCAM-1+, THY-1+, STRO-2+, STRO-4+ (HSP-90β) and/or CD146+. For example, the cells are selected for one or more of the foregoing markers and/or shown to express one or more of the foregoing markers. In this regard, a cell shown to express a marker need not be specifically tested, rather previously enriched or isolated cells can be tested and subsequently used, isolated or enriched cells can be reasonably assumed to also express the same marker.

In one example, the STRO-1$^{bright}$ cells are perivascular mesenchymal precursor cells as defined in WO 2004/85630, characterized by the presence of the perivascular marker 3G5.

A cell that is referred to as being "positive" for a given marker may express either a low (lo or dim) or a high (bright, bri) level of that marker depending on the degree to which the marker is present on the cell surface, where the terms relate to intensity of fluorescence or other marker used in the sorting process of the cells. The distinction of lo (or dim or dull) and bri will be understood in the context of the marker used on a particular cell population being sorted. A cell that is referred to as being "negative" for a given marker is not necessarily completely absent from that cell. This term means that the marker is expressed at a relatively very low level by that cell, and that it generates a very low signal when detectably labeled or is undetectable above background levels, for example, levels detected using an isotype control antibody.

The term "bright" or bri as used herein, refers to a marker on a cell surface that generates a relatively high signal when detectably labeled. Whilst not wishing to be limited by theory, it is proposed that "bright" cells express more of the target marker protein (for example, the antigen recognized by a STRO-1 antibody) than other cells in the sample. For instance, STRO-1$^{bri}$ cells produce a greater fluorescent signal, when labeled with a FITC-conjugated STRO-1 antibody as determined by fluorescence activated cell sorting (FACS) analysis, than non-bright cells (STRO-1$^{dull/dim}$). In one example, the mesenchymal lineage precursor or stem cells are isolated from bone marrow and enriched for by selection of STRO-1+ cells. In this example, "bright" cells constitute at least about 0.1% of the most brightly labeled bone marrow mononuclear cells contained in the starting sample. In other examples, "bright" cells constitute at least about 0.1%, at least about 0.5%, at least about 1%, at least about 1.5%, or at least about 2%, of the most brightly labeled bone marrow mononuclear cells contained in the starting sample. In an example, STRO-1$^{bright}$ cells have 2 log magnitude higher expression of STRO-1 surface expression relative to "background", namely cells that are STRO-1−. By comparison, STRO-1$^{dim}$ and/or STRO-1$^{intermediate}$ cells have less than 2 log magnitude higher expression of STRO-1 surface expression, typically about 1 log or less than "background".

As used herein the term "TNAP" is intended to encompass all isoforms of tissue non-specific alkaline phosphatase. For example, the term encompasses the liver isoform (LAP), the bone isoform (BAP) and the kidney isoform (KAP). In one example, the TNAP is BAP. In one example, TNAP refers to a molecule which can bind the STRO-3 antibody produced by the hybridoma cell line deposited with ATCC on 19 Dec. 2005 under the provisions of the Budapest Treaty under deposit accession number PTA-7282.

Furthermore, in one example, the STRO-1+ cells are capable of giving rise to clonogenic CFU-F.

In one example, a significant proportion of the STRO-1+ cells are capable of differentiation into at least two different germ lines. Non-limiting examples of the lineages to which the cells may be committed include bone precursor cells; hepatocyte progenitors, which are multipotent for bile duct epithelial cells and hepatocytes; neural restricted cells, which can generate glial cell precursors that progress to oligodendrocytes and astrocytes; neuronal precursors that progress to neurons; precursors for cardiac muscle and cardiomyocytes, glucose-responsive insulin secreting pancreatic beta cell lines. Other lineages include, but are not limited to, odontoblasts, dentin-producing cells and chondrocytes, and precursor cells of the following: retinal pigment epithelial cells, fibroblasts, skin cells such as keratinocytes, dendritic cells, hair follicle cells, renal duct epithelial cells, smooth and skeletal muscle cells, testicular progenitors, vascular endothelial cells, tendon, ligament, cartilage, adipocyte, fibroblast, marrow stroma, cardiac muscle, smooth muscle, skeletal muscle, pericyte, vascular, epithelial, glial, neuronal, astrocyte and oligodendrocyte cells.

In one example, the mesenchymal lineage precursor or stem cells are MSCs. The MSCs may be a homogeneous composition or may be a mixed cell population enriched in MSCs. Homogeneous MSC compositions may be obtained by culturing adherent marrow or periosteal cells, and the MSCs may be identified by specific cell surface markers which are identified with unique monoclonal antibodies. A method for obtaining a cell population enriched in MSCs is described, for example, in U.S. Pat. No. 5,486,359. Alternative sources for MSCs include, but are not limited to, blood, skin, cord blood, muscle, fat, bone, and perichondrium.

The isolated or enriched mesenchymal lineage precursor or stem cells can be expanded in vitro by culture. As will be appreciated by those skilled in the art, the isolated or enriched mesenchymal lineage precursor or stem cells can be cryopreserved, thawed and subsequently expanded in vitro by culture.

In one example, the isolated or enriched or cultured mesenchymal lineage precursor or stem cells are seeded at 50,000 viable cells/cm$^2$ in serum-supplemented culture medium, for example, alpha minimum essential media (αMEM) supplemented with 10% fetal bovine serum (FBS) and glutamine, and allowed to adhere to the culture vessel overnight at 37° C., 20% 02. The culture medium is subsequently replaced with Chondrogenic Basal Medium (CBM; Lonza, Walkersville, Md.) supplemented with 0.5% bovine serum albumin (BSA) and the cells cultured for a further 68 to 72 hours at 37° C., 5% $O_2$ prior to determining the amount of TGFβ1 released by the cells into the culture medium.

The cultured mesenchymal lineage precursor or stem cells are phenotypically different to cells in vivo. For example, in one embodiment they express one or more of the following markers, CD44, NG2, DC146 and CD140b.

The cultured mesenchymal lineage precursor or stem cells are biologically different to cells in vivo, having a higher rate of proliferation compared to the largely non-cycling (quiescent) cells in vivo.

The mesenchymal lineage precursor or stem cells may be cryopreserved prior to administration to a subject.

Determining the Amount of TGFβ1 Levels

The present disclosure contemplates any form of assay, including Western blot, enzyme-linked immunosorbent assay (ELISA), fluorescence-linked immunosorbent assay (FLISA), competition assay, radioimmunoassay, lateral flow immunoassay, flow-through immunoassay, electrochemiluminescent assay, nephelometric-based assays, turbidometric-based assay, fluorescence activated cell sorting (FACS)-based assays for detection of TGFβ1 in culture medium used to culture mesenchymal lineage or precursor cells, and surface plasmon resonance (SPR or Biacore).

One form of a suitable assay is, for example, an ELISA or FLISA.

In one form, such an assay involves immobilizing a TGFβ1 binding protein onto a solid matrix, such as, for example a polystyrene or polycarbonate microwell or dipstick, a membrane, or a glass support (e.g., a glass slide). A test sample is then brought into direct contact with the TGFβ1 binding protein and TGFβ1 in the sample is bound or captured. Following washing to remove any unbound protein in the sample, a protein that binds to TGFβ1 at a distinct epitope is brought into direct contact with the captured TGFβ1. This detector protein is generally labelled with a detectable reporter molecule, such as, for example, an enzyme (e.g. horseradish peroxidase (HRP)), alkaline phosphatase (AP) or β-galactosidase) in the case of an ELISA or a fluorophore in the case of a FLISA. Alternatively, a second labeled protein can be used that binds to the detector protein. Following washing to remove any unbound protein the detectable reporter molecule is detected by the addition of a substrate in the case of an ELISA, such as, for example, hydrogen peroxide, TMB, or toluidine, or 5-bromo-4-chloro-3-indol-beta-D-galactopyranoside (x-gal). Of course, the immobilized (capture) protein and the detector protein may be used in the opposite manner.

The level of the antigen in the sample is then determined using a standard curve that has been produced using known quantities of the marker or by comparison to a control sample.

The assays described above are readily modified to use chemiluminescence or electrochemiluminescence as the basis for detection.

As will be apparent to the skilled person, other detection methods based on an immunosorbent assay are useful in the performance of the present disclosure. For example, an immunosorbent method based on the description above using a radiolabel for detection, or a gold label (e.g., colloidal gold) for detection, or a liposome, for example, encapsulating NAD+ for detection or an acridinium linked immunosorbent assay.

In some examples of the disclosure, the level of TGFβ1 is determined using a surface plasmon resonance detector (e.g., BIAcore™, GE Healthcare, Piscataway, N.J.), a flow through device (e.g., as described in U.S. Pat. No. 7,205,159), a micro- or nano-immunoassay device (e.g., as described in U.S. Pat. No. 7,271,007), a lateral flow device (e.g., as described in US publication 20040228761 or US publication 20040265926), a fluorescence polarization immunoassay (FPIA, e.g., as described in U.S. Pat. No. 4,593,089 or 4,751,190), or an immunoturbidimetric assay (e.g., as described in U.S. Pat. No. 5,571,728 or 6,248,597).

Compositions and Administration

A composition comprising mesenchymal lineage precursor or stem cells may be prepared in a pharmaceutically acceptable carrier. The term "pharmaceutically acceptable carrier" as used herein refers to compositions of matter that facilitate the storage, administration, and/or maintain the biological activity of the mesenchymal lineage precursor or stem cells.

In one example, the carrier does not produce significant local or systemic adverse effect in the recipient. The pharmaceutically acceptable carrier may be solid or liquid. Useful examples of pharmaceutically acceptable carriers include, but are not limited to, diluents, solvents, surfactants, excipients, suspending agents, buffering agents, lubricating agents, adjuvants, vehicles, emulsifiers, absorbants, dispersion media, coatings, stabilizers, protective colloids, adhesives, thickeners, thixotropic agents, penetration agents, sequestering agents, scaffolds, isotonic and absorption delaying agents that do not affect the viability and activity of the mesenchymal lineage precursor or stem cells. The selection of a suitable carrier is within the skill of those skilled in the art.

Suitable pharmaceutical carriers include, but are not limited to, hyaluronan, chemically modified hyaluronan, saline, phosphate buffered saline, chondroitin sulfate, glucosamine, mannosamine, proteoglycan, proteoglycan fragments, chitin, chitosan, or other polysaccharide or polymer material.

Mesenchymal lineage precursor or stem cells can also be incorporated or embedded within scaffolds. Suitable scaffolds include but are not limited to, biological, degradable scaffolds. Natural biodegradable scaffolds include but are not limited to, collagen, fibronectin, and laminin scaffolds. Synthetic biodegradable scaffolds include but are not limited to, polyglycolic acid scaffolds (e.g., as described by (Vacanti, Morse, & Saltzman, 1988) (Cima, Ingber, Vacanti, & Langer, 1991) (Vacanti, Langer, Schloo, & Vacanti, 1991)), synthetic polymers such as, for example, polyanhydrides, polyorthoesters, and polylactic acid; and gelatin resorbable sponges such as, for example, Gelform™ (Pfizer).

Compositions of the disclosure may conveniently be presented in unit dosage form and may be prepared by any of the methods well known in the art. The term "dosage unit form" as used herein refers to physically discrete units suited as unitary dosages for subjects to be treated; each unit containing a predetermined quantity of active compound calculated to produce the desired therapeutic or prophylactic effect in association with the pharmaceutical carrier. The dose of mesenchymal lineage precursor or stem cells may vary according to factors such as the disease state, age, sex, and weight of the subject to be treated.

Exemplary doses include at least about $1 \times 10^6$ cells. For example, a dose can comprise between about $1.0 \times 10^6$ to about $1 \times 10^{10}$ cells, for example, between about $1.1 \times 10^6$ to about $1 \times 10^9$ cells, for example, between about $1.2 \times 10^6$ to about $1 \times 10^8$ cells, for example, between about $1.3 \times 10^6$ to about $1 \times 10^7$ cells, for example, between about $1.4 \times 10^6$ to about $9 \times 10^6$ cells, for example, between about $1.5 \times 10^6$ to about $8 \times 10^6$ cells, for example, between about $1.6 \times 10^6$ to about $7 \times 10^6$ cells, for example, between about $1.7 \times 10^6$ to about $6 \times 10^6$ cells, for example, between about $1.8 \times 10^6$ to about $5 \times 10^6$ cells, for example, between about $1.9 \times 10^6$ to about $4 \times 10^6$ cells, for example, between about $2 \times 10^6$ to about $3 \times 10^6$ cells.

In one example, the dose comprises between about $5 \times 10^5$ to $2 \times 10^7$ cells, for example, between about $6 \times 10^6$ cells to about $1.8 \times 10^7$ cells. The dose may be, for example, about $6 \times 10^6$ cells or about $1.8 \times 10^7$ cells.

The mesenchymal lineage precursor or stem cells comprise at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95% of the cell population of the composition.

Compositions of the disclosure may be cryopreserved. Cryopreservation of mesenchymal lineage precursor or stem cells can be carried out using slow-rate cooling methods or 'fast' freezing protocols known in the art. Preferably, the method of cryopreservation maintains similar phenotypes, cell surface markers and growth rates of cryopreserved cells in comparison with unfrozen cells.

The cryopreserved composition may comprise a cryopreservation solution. The pH of the cryopreservation solution is typically 6.5 to 8, preferably 7.4.

The cryopreservation solution may comprise a sterile, non-pyrogenic isotonic solution such as, for example, PlasmaLyte A™. 100 mL of PlasmaLyte A™ contains 526 mg of sodium chloride, USP (NaCl); 502 mg of sodium gluconate ($C_6H_{11}NaO_7$); 368 mg of sodium acetate trihydrate, USP ($C_2H_3NaO_2.3H_2O$); 37 mg of potassium chloride, USP (KCl); and 30 mg of magnesium chloride, USP ($MgCl_2.6H_2O$). It contains no antimicrobial agents. The pH is adjusted with sodium hydroxide. The pH is 7.4 (6.5 to 8.0).

The cryopreservation solution may comprise Profreeze™. The cryopreservation solution may additionally or alternatively comprise culture medium, for example, αMEM.

To facilitate freezing, a cryoprotectant such as, for example, dimethylsulfoxide (DMSO), is usually added to the cryopreservation solution. Ideally, the cryoprotectant should be nontoxic for cells and patients, nonantigenic, chemically inert, provide high survival rate after thawing and allow transplantation without washing. However, the most commonly used cryoprotector, DMSO, shows some cytotoxicity. Hydroxylethyl starch (HES) may be used as a substitute or in combination with DMSO to reduce cytotoxicity of the cryopreservation solution.

The cryopreservation solution may comprise one or more of DMSO, hydroxyethyl starch, human serum components and other protein bulking agents. In one example, the cryopreserved solution comprises about 5% human serum albumin (HSA) and about 10% DMSO. The cryopreservation solution may further comprise one or more of methylcellulose, polyvinyl pyrrolidone (PVP) and trehalose.

In one embodiment, cells are suspended in 42.5% Profreeze™/50% αMEM/7.5% DMSO and cooled in a controlled-rate freezer.

The cryopreserved composition may be thawed and administered directly to the subject or added to another solution, for example, comprising HA. Alternatively, the cryopreserved composition may be thawed and the mesenchymal lineage precursor or stem cells resuspended in an alternate carrier prior to administration.

Compositions of the disclosure can be administered by a route that is suitable for the particular disease state to be treated. For example, compositions of the disclosure can be administered systemically, i.e., parenterally, intravenously or by injection. Compositions of the disclosure can be targeted to a particular tissue or organ.

Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage.

In some embodiments, it may not be necessary or desirable to immunosuppress a patient prior to initiation of therapy with cellular compositions. Indeed, transplantation of allogeneic STRO-1+ cells in sheep was well tolerated in the absence of immunosuppression. However, in other instances it may be desirable or appropriate to pharmacologically immunosuppress a patient prior to initiating cell therapy. This may be accomplished through the use of systemic or local immunosuppressive agents, or it may be accomplished by delivering the cells in an encapsulated device. The cells may be encapsulated in a capsule that is permeable to nutrients and oxygen required by the cell and therapeutic factors the cell is yet impermeable to immune humoral factors and cells. Preferably the encapsulant is hypoallergenic, is easily and stably situated in a target tissue, and provides added protection to the implanted structure. These and other means for reducing or eliminating an immune response to the transplanted cells are known in the art. As an alternative, the cells may be genetically modified to reduce their immunogenicity.

It will be appreciated that the mesenchymal lineage precursor or stem cells may be administered with other beneficial drugs or biological molecules (growth factors, trophic factors). When administered with other agents, they may be administered together in a single pharmaceutical composition, or in separate pharmaceutical compositions, simultaneously or sequentially with the other agents (either before or after administration of the other agents). Bioactive factors which may be co-administered include anti-apoptotic agents (e.g., EPO, EPO mimetibody, TPO, IGF-I and IGF-II, HGF, caspase inhibitors); anti-inflammatory agents (e.g., p38 MAPK inhibitors, TGF-beta inhibitors, statins, IL-6 and IL-1 inhibitors, PEMIROLAST™, TRANILAST™, REMICADE™, SIROLIMUS™, and non-steroidal anti-inflammatory drugs (NSAIDs) such as TEPOXALIN™, TOLMETIN™, SUPROFEN™); immunosupressive/immunomodulatory agents (e.g., calcineurin inhibitors such as cyclosporine, tacrolimus); mTOR inhibitors (e.g., SIROLIMUS™, EVEROLIMUS™); anti-proliferatives (e.g., azathioprine, mycophenolate mofetil); corticosteroids (e.g., prednisolone, hydrocortisone); antibodies such as monoclonal anti-IL-2Ralpha receptor antibodies (e.g., basiliximab, daclizumab), polyclonal anti-T-cell antibodies (e.g., antithymocyte globulin (ATG); anti-lymphocyte globulin (ALG); monoclonal anti-T cell antibody OKT3)); antithrombogenic agents (e.g., heparin, heparin derivatives, urokinase, PPack (dextrophenylalanine proline arginine chloromethylketone), antithrombin compounds, platelet receptor antagonists, anti-thrombin antibodies, anti-platelet receptor antibodies, aspirin, dipyridamole, protamine, hirudin, prostaglandin inhibitors, and platelet inhibitors); and anti-oxidants (e.g., probucol, vitamin A, ascorbic acid, tocopherol, coenzyme Q-10, glutathione, L-cysteine, N-acetylcysteine) as well as local anesthetics.

Treatment of Degenerative Disc Disease

The intervertebral disc (IVD) is a functional unit connecting the vertebral bodies of the spine and is responsible for shock absorption and mobility of the spinal unit (Raj, 2008). It is composed of a central nucleus pulposus (NP) and a peripheral annulus fibrosus (AF), and is separated from the vertebral bodies by two cartilaginous endplates (EP) (FIG. 1). The NP forms the gelatinous inner core of the IVD. It comprises an irregular mesh of type II collagen fibers together with large quantities of the proteoglycan aggrecan which, with its high anionic glycosaminoglycan (GAG) content and binding of water provides tissue viscoelasticity, stiffness and resistance to compression (Watanabe, Yamada, & Kimata, 1998). The AF is subdivided into outer AF, which is formed by distinct lamellae, composed of type I collagen fibers oriented obliquely between each lamellae (Marchand & Ahmed, 1990) and a less fibrous and less organized inner AF, characterized by a transition to type II collagen and increased proteoglycan content (Humzah & Soames, 1988). This architecture enables the AF to constrain the hydrostatic pressures generated within the NP upon compression, facilitating mobility between the spinal segments (Guerin & Elliott, 2007) (Schmidt, Kettler, Heuer, Simon, Claes, & Wilke, 2007). With the exception of the outermost AF, the IVD is aneural (Roberts, Eisenstein, Menage, Evans, & Ashton, 1995) and is practically devoid of blood vessels (Crock & Goldwasser, 1984) and consequently is reliant upon diffusion through the EP for nutrient and oxygen supply (Urban, Smith, & Fairbank, 2004). Homeostasis of the IVD as a unit necessitates optimal function of all 3 structures and impairment of one or more of these structures can lead to IVD degeneration.

The integrity of the IVD is maintained by a fine balance of the activity of cytokines, growth factors, enzymes, and enzyme inhibitors, in a paracrine and/or autocrine fashion that collectively regulate the balance between extracellular matrix (ECM) synthesis/apposition and degradation.

In IVD degeneration, perturbation of this delicate balance is triggered by multiple etiological factors (such as aging, infection, smoking, genetic disposition, abnormal biomechanical loading or IVD nutritional status) (Roberts, Evans, Trivedi, & Menage, 2006) (Cheung, et al., 2009). Although not necessarily the primary site of the defect, histopathological changes are first observed in the NP with evidence of increased breakdown of ECM, altered matrix synthesis (consisting largely of a switch from type II to type I collagen production and decreased synthesis of aggrecan) and cell loss through apoptosis and in situ replication of surviving cells to form clusters (Adams & Roughley, 2006) (Johnson & Roberts, 2007) (Le Maitre, Pockert, Buttle, Freemont, & Hoyland, 2007). The consequent loss of swelling pressure in the NP leads to a loss of the normal balance of forces between the NP and AF and extension of the degenerative process to the AF, resulting in microtrauma ('tears') allowing blood vessels and nerves a route into the IVD (Hilton & Ball, 1984) leading to the generation of pain associated with degenerative disc disease.

Irrespective of the specific initiating event, IVD degeneration is believed to be mediated by abnormal synthesis and secretion of proinflammatory molecules by both the endogenous NP cells (NPCs) and AF cells (AFCs) and by non-resident cells of the immune system such as macrophages and T-cells (reviewed by (Freemont, 2009) (Risbud & Shapiro, 2014)). Secreted proinflammatory mediators of disc degeneration include tumor necrosis factor $\alpha$ (TNF$\alpha$), interleukin (IL)-1$\beta$, IL-6, IL-17 and IL-17 in addition to various chemokines (Risbud & Shapiro, 2014) (Seguin, Pilliar, Roughley, & Kandel, 2005) (Le Maitre, Hoyland, & Freemont, 2007) (Shamji, et al., 2010) (Purmessur, Walter, Roughley, Laudier, Hecht, & Iatridis, 2013) amongst which the roles of TNF$\alpha$ and IL-1$\beta$ are the most extensively studied. Both cytokines induce upregulation of genes involved in ECM degradation (Le Maitre, Hoyland, & Freemont, 2007) (Le Maitre, Freemont, & Hoyland, 2005) (Le Maitre, Hoyland, & Freemont, 2007). Both IL-$\beta$ and its receptor are upregulated in degenerated IVD tissue (Le Maitre, Hoyland, & Freemont, 2007) (Le Maitre, Hoyland, & Freemont, 2007) while expression of TNF$\alpha$ has also been implicated in neurite ingrowth and irritation (Murata, Onda, Rydevik, Takahashi, & Olmarker, 2006) (Wang, Markova, Anderson, Zheng, Shapiro, & Risbud, 2011).

In one embodiment, mesenchymal lineage precursor or stem cells are injected into a NP to restore normal mechanical and or physiological properties to a damaged intervertbral disc.

Numerous biologic and synthetic materials are contemplated for co-injection with the mesenchymal lineage precursor or stem cells into a NP. For example, one or more natural or synthetic glycosaminoglycans (GAGs) or mucopolysaccharides, such as, for example, hyaluronan (hyaluronic acid; HA), chondroitan sulfate, dermatan sulfate, keratin sulfate, heparin, heparin sulfate, galactosaminoglycuronglycan sulfate (GGGS), including their physiological salts, may be injected directly into the NP. It has been suggested that HA plays a role in the stimulation of endogenous HA synthesis by synovial cells and proteoglycan synthesis by chondrocytes, inhibits the release of chondrodegradative enzymes, and acts as a scavenger of oxygen free radicals known to play part in cartilage deterioration. Chondroitin sulfate and glucosamine injectables have similarly been shown to block the progression of articular cartilage degeneration. Arguably, other GAG's may provide similar protective or restorative properties having therapeutic value making them ideal candidates for injection into a disc undergoing DDD. Another valuable property of GAG's is their strong ability to attract and retain water. Thus, it may be appropriate to mix GAG's with water or other aqueous materials to form a viscous gel that may then be injected into the space created from aspiration of a NP, or alternatively, added to an existing NP as a supplement. Natural "hydrogels" can thereby be formed which are capable of filling space in three dimensions and acting like packing materials that resist crushing and enable a disc to adequately absorb the shock associated with movement.

Synthetic hyaluronic gels such as, for example, Euflexxa®, (Ferring Pharmaceuticals) or Restylane™. (Q-Med Aktiebolag Co., Sweden) are also suitable for use.

Examples of other injectable synthetic materials that may be used for co-administration include medical grade silicone, Bioplastique™ (solid silicone particles suspended in polyvinylpyrrolidone carrier; Uroplasty BV, Netherlands), Arteplast™ (microspheres of polymethylmethacrylate (PMMA) suspended in gelatin carrier; Artes Medical, USA), Artecoll™ (smooth PMMA spheres suspended in bovine cartilage carrier; Artepharma Pharmazeu Tische, GMBH Co., Germany). Further, synthetic hydrogel compositions may be employed as a filler material to restore normal shape to a disc, thereby restoring normal bio-mechanical functions.

Antioxidants having known chondroprotective abilities are also candidates for injection into the NP. Examples of these include tocophereol (vitamin E), superoxide dismutase (SOD), ascorbate (vitamin C), catalase and others. Further, amphiphilic derivatives of sodium alginate and the like are also contemplated herein for injection. Additionally, recombinant osteogenic protein-1 (OP-1) is a good candidate for injection because of its ability to promote the formation of a proteoglycan rich matrix by NPCs and AFCs.

Use of synthetic injectables is also contemplated. These are particularly applicable to situations where the primary goal is to restore bio-mechanical function to a disc.

HA alone or in combination with other GAGs may be used as a carrier to deliver mesenchymal lineage precursor or stem cells. The concentration and viscosity of the HA/GAG composition can be routinely determined. In one embodiment, the composition comprises at least about 0.5% HA or HA salt. For example, a population of cells comprising mesenchymal lineage precursor or stem cells could be suspended in Euflexxa™ (1% sodium hyaluronate) at a 1:1 ratio.

In another example, the mesenchymal lineage precursor or stem cells may be delivered in admixture with fibrin glue. The term "fibrin glue" as used herein refers to the insoluble matrix formed by the cross-linking of fibrin polymers in the presence of calcium ions. The fibrin glue may be formed from fibrinogen, or a derivative or metabolite thereof, fibrin (soluble monomers or polymers) and/or complexes thereof derived from biological tissue or fluid which forms a fibrin matrix. Alternatively, the fibrin glue may be formed from fibrinogen, or a derivative or metabolite thereof, or fibrin, produced by recombinant DNA technology.

The fibrin glue may also be formed by the interaction of fibrinogen and a catalyst of fibrin glue formation (such as thrombin and/or Factor XIII). As will be appreciated by those skilled in the art, fibrinogen is proteolytically cleaved in the presence of a catalyst (such as thrombin) and converted to a fibrin monomer. The fibrin monomers may then form polymers which may cross-link to form a fibrin glue matrix. The cross-linking of fibrin polymers may be enhanced by the presence of a catalyst such as Factor XIII. The catalyst of fibrin glue formation may be derived from blood plasma, cryoprecipitate or other plasma fractions containing fibrinogen or thrombin. Alternatively, the catalyst may be produced by recombinant DNA technology.

Combining fibrinogen with thrombin leads to clot formation. The rate at which the clot forms is dependent upon the concentration of thrombin mixed with fibrinogen. Being an enzyme dependent reaction, the higher the temperature (up to 37° C.) the faster the clot formation rate. The tensile strength of the clot is dependent upon the concentration of fibrinogen used.

When the fibrin clot is generated in the presence of HA it undergoes interactions and becomes interdigitated with the cross-linked matrix. This matrix is known to play a major role in tissue regeneration and performs cell regulatory functions in tissue repair (Weigel, Fuller, & Le Boeuf, 1986). The dissolution rate of HA is also prolonged in the HA-Fibrin matrix which could be beneficial in prolonging the therapeutic effects of this GAG (Wadstrom & Tengblad, 1993).

Several publications describe the use of fibrin glue for the delivery of therapeutic agents. For example, U.S. Pat. No. 4,983,393 discloses a composition for use as an intra-vaginal insert comprising agarose, agar, saline solution glycosaminoglycans, collagen, fibrin and an enzyme. Further, U.S. Pat. No. 3,089,815 discloses an injectable pharmaceutical preparation composed of fibrinogen and thrombin and U.S. Pat. No. 6,468,527 discloses a fibrin glue which facilitates the delivery of various biological and non-biological agents to specific sites within the body.

Compositions of the disclosure can be "surgically added" to the disc space. That is, compositions can be added by the intervention of medical personnel, as distinguished from being "added" by the body's natural growth or regeneration processes. The surgical procedure preferably includes injection through a hypodermic needle, although other surgical methods of introducing the composition into the disc may be used. For example, the composition may be introduced into a disc by extrusion through a dilated annular opening, infusion through a catheter, insertion through an opening created by trauma or surgical incision, or by other means of invasive or minimally invasive deposition of the composition into the disc space.

Genetically-Modified Cells

In one embodiment, the mesenchymal lineage precursor or stem cells are genetically modified, for example, to express and/or secrete a protein of interest, for example, a protein providing a therapeutic and/or prophylactic benefit, for example, insulin, glucagon, somatostatin, trypsinogen, chymotrypsinogen, elastase, carboxypeptidase, pancreatic lipase or amylase or a polypeptide associated with or causative of enhanced angiogenesis or a polypeptide associated with differentiation of a cell into a pancreatic cell or a vascular cell.

Methods for genetically modifying a cell will be apparent to the skilled person. For example, a nucleic acid that is to be expressed in a cell is operably-linked to a promoter for inducing expression in the cell. For example, the nucleic acid is linked to a promoter operable in a variety of cells of a subject, such as, for example, a viral promoter, for example, a CMV promoter (e.g., a CMV-IE promoter) or a SV-40 promoter. Additional suitable promoters are known in the art.

Preferably, the nucleic acid is provided in the form of an expression construct. The term "expression construct" as used herein refers to a nucleic acid that has the ability to confer expression on a nucleic acid (e.g., a reporter gene and/or a counter-selectable reporter gene) to which it is operably connected, in a cell. Within the context of the present disclosure, it is to be understood that an expression construct may comprise or be a plasmid, bacteriophage, phagemid, cosmid, virus sub-genomic or genomic fragment, or other nucleic acid capable of maintaining and/or replicating heterologous DNA in an expressible format.

Methods for the construction of a suitable expression construct for performance of the invention will be apparent to the skilled person and are described, for example, in (Ausubel F. M., 1987 including all updates untill present) or (Sambrook & Green, 2012). For example, each of the components of the expression construct is amplified from a suitable template nucleic acid using, for example, PCR and subsequently cloned into a suitable expression construct, such as, for example, a plasmid or a phagemid.

Vectors suitable for such an expression construct are known in the art and/or described herein. For example, an expression vector suitable for the method of the present invention in a mammalian cell is, for example, a vector of the pcDNA vector suite (Invitrogen), a vector of the pCI vector suite (Promega), a vector of the pCMV vector suite (Clontech), a pM vector (Clontech), a pSI vector (Promega), a VP 16 vector (Clontech), or a vector of the pcDNA vector suite (Invitrogen).

The skilled person will be aware of additional vectors and sources of such vectors, such as, for example, Invitrogen Corporation, Clontech or Promega.

Means for introducing the isolated nucleic acid molecule or a gene construct comprising same into a cell for expression are known to those skilled in the art. The technique used for a given organism depends on the known successful techniques. Means for introducing recombinant DNA into cells include microinjection, transfection mediated by DEAE-dextran, transfection mediated by liposomes such as by using lipofectamine (Gibco, MD, USA) and/or cellfectin (Gibco, MD, USA), PEG-mediated DNA uptake, electroporation and microparticle bombardment such as by using DNA-coated tungsten or gold particles (Agracetus Inc., WI, USA) amongst others.

Alternatively, an expression construct of the invention is a viral vector. Suitable viral vectors are known in the art and commercially available. Conventional viral-based systems for the delivery of a nucleic acid and integration of that nucleic acid into a host cell genome include, for example, a retroviral vector, a lentiviral vector or an adeno-associated viral vector. Alternatively, an adenoviral vector is useful for introducing a nucleic acid that remains episomal into a host cell. Viral vectors are an efficient and versatile method of gene transfer in target cells and tissues. Additionally, high transduction efficiencies have been observed in many different cell types and target tissues.

For example, a retroviral vector generally comprises cis-acting long terminal repeats (LTRs) with packaging capacity for up to 6-10 kb of foreign sequence. The minimum cis-acting LTRs are sufficient for replication and packaging of a vector, which is then used to integrate the expression construct into the target cell to provide long term expression. Widely used retroviral vectors include those based upon murine leukemia virus (MuLV), gibbon ape leukemia virus (GaLV), simian immunodeficiency virus (SrV), human immunodeficiency virus (HIV), and combinations thereof (see, e.g., International publication WO1994/026877, (Buchschacher & Panganiban, 1992) (Johann, Gibbons, & O'Hara, 1992) (Sommerfelt & Weiss, 1990) (Wilson, Reitz, Okayama, & Eiden, 1989) (Miller, Garcia, von Suhr, Lynch, Wilson, & Eiden, 1991) (Miller & Rosman, 1989) (Miller, 1990) (Scarpa, Cournoyer, Munzy, Moore, Belmont, & Caskey, 1991) (Burns, Friedmann, Driever, Burrascano, & Yee, 1993)).

Various adeno-associated virus (AAV) vector systems have also been developed for nucleic acid delivery. AAV vectors can be readily constructed using techniques known in the art. (see, e.g., U.S. Pat. Nos. 5,173,414 and 5,139,941, International publications WO 92/01070 and WO 93/03769, (Lebkowski, McNally, Okarma, & Lerch, 1988) (Vincent, Moore, & Haigwood, 1990) (Carter, 1992) (Muzyczka, 1992); (Kotin, 1994) (Shelling & Smith, 1994) (Zhou, et al., 1994)).

Additional viral vectors useful for delivering an expression construct of the invention include, for example, those derived from the pox family of viruses, such as vaccinia virus and avian poxvirus or an alphavirus or a conjugate virus vector (e.g., that described in (Fisher-Hoch, et al., 1989)).

Example 1 Materials and Methods

Immunoselection of MPCs by Selection of STRO-3+ Cells

Bone marrow (BM) is harvested from healthy normal adult volunteers (20-35 years old). Briefly, 40 ml of BM is aspirated from the posterior iliac crest into lithium-heparin anticoagulant-containing tubes.

BM mononuclear cells (BMMNC) are prepared by density gradient separation using Lymphoprep™ (Nycomed Pharma, Oslo, Norway) as previously described (Zannettino, Buhring, Niutta, Watt, Benton, & Simmons, 1998). Following centrifugation at 400×g for 30 minutes at 4° C., the buffy layer is removed with a transfer pipette and washed three times in "HHF", composed of Hank's balanced salt solution (HBSS; Life Technologies, Gaithersburg, Md.), containing 5% fetal calf serum (FCS, CSL Limited, Victoria, Australia).

STRO-3+(or TNAP+) cells were subsequently isolated by magnetic activated cell sorting as previously described (Gronthos & Simmons, 1995) (Gronthos, 2003). Briefly, approximately 1-3×10$^8$ BMMNC are incubated in blocking buffer, consisting of 10% (v/v) normal rabbit serum in HHF for 20 minutes on ice. The cells are incubated with 200 μl of a 10 μg/ml solution of STRO-3 mAb in blocking buffer for 1 hour on ice. The cells are subsequently washed twice in HHF by centrifugation at 400×g. A 1/50 dilution of goat anti-mouse γ-biotin (Southern Biotechnology Associates, Birmingham, UK) in HHF buffer is added and the cells incubated for 1 hour on ice. Cells are washed twice in MACS buffer ($Ca^{2+}$- and $Mg^{2+}$-free PBS supplemented with 1% BSA, 5 mM EDTA and 0.01% sodium azide) as above and resuspended in a final volume of 0.9 ml MACS buffer.

One hundred μl streptavidin microbeads (Miltenyi Biotec; Bergisch Gladbach, Germany) are added to the cell suspension and incubated on ice for 15 min. The cell suspension is washed twice and resuspended in 0.5 ml of MACS buffer and subsequently loaded onto a mini MACS column (MS Columns, Miltenyi Biotec), and washed three times with 0.5 ml MACS buffer to retrieve the cells which did not bind the STRO-3 mAb (deposited on 19 Dec. 2005 with American Type Culture Collection (ATCC) under accession number PTA-7282—see International publication WO 2006/

108229). After addition of a further 1 ml MACS buffer, the column is removed from the magnet and the TNAP+ cells are isolated by positive pressure. An aliquot of cells from each fraction can be stained with streptavidin-FITC and the purity assessed by flow cytometry.

The mesenchymal precursor cells (MPCs) isolated in this manner are STRO-1$^{bright}$ MPCs.

Generation of MPC CM

Conditioned Medium (CM) was generated from available MPC product lots (263873, 22-12-001US, 22-12-02US, 345938, 2011CC053, 2011CCO11, 2012CC010, 322509, 376232, 376233, 380505, 380507, 385470, 385471, 1857469) and represent different donors and clinical and product development manufacturing runs. Cryopreserved MPC product was thawed and cells were seeded at 50,000 cells/cm$^2$ in serum-supplemented growth medium and allowed to adhere overnight at 37° C., 20% 02. To generate CM compatible with disc cell-based functional assays, MPC growth medium was replaced with Chondrogenic Basal Medium (CBM; Lonza, Walkersville, Md.) supplemented only with 0.5% bovine serum albumin (BSA) at a volume of 209 µl medium/cm$^2$ and cells were cultured for 3 days at 37° C., 5% 02. At the end of this culture period, medium was collected and centrifuged to remove any cells in suspension, and the resulting supernatant was collected and stored at −80° C. until use.

Bioassay for NPC Proliferation

Nucleus pulposus cell (NPC) proliferation in response to MPC CM was assessed by quantification of DNA incorporation of 5-ethynyl-2'-deoxyuridine (EdU) in actively dividing cells. Human NPCs were seeded onto poly-L-lysine-coated culture dishes at 2,500 cells/cm$^2$ in serum-containing growth medium. Cells were allowed to adhere overnight by incubation at 37° C., 5% 02, then serum-starved for 48 h. Following serum-deprivation, cells were stimulated with MPC CM for 48 h. EdU was added to cells for the last 18 h of culture according to the manufacturer's instructions (Click-iT™ Kit, Invitrogen, Carlsbad, Calif.). Subsequently, cells were detached with trypsin and stained for viability. Cells were then fixed and stained for EdU incorporation and analyzed by flow cytometry. EdU$^+$ cells within the viable population were identified relative to control cells that were not stained with EdU.

Bioassay for NPC Proteoglycan Synthesis

The effects of MPC CM on NPC matrix production in vitro were examined by semi-quantitative measurement of Alcian blue dye extracted from micromass cultures following staining of proteoglycans deposited within the extracellular matrix (ECM). To establish human NP micromass cultures, NPC were seeded in high density 2-dimensional (2D) cultures by adding a 10 µl drop of growth medium containing 100,000 cells to each well of a 48 well plate coated with human fibronectin at 5 µg/cm$^2$. Cells were allowed to adhere for 2 h followed by the addition of complete growth media to flood the well and overnight incubation of cells. On the following day, cells were washed once in warm PBS and serum-starved for 48 h prior to stimulation with MPC CM for 7 days. At the end of the culture period, cells were fixed in 10% zinc formalin in situ and stained with Alcian blue to detect proteoglycans. Digital images of representative wells were captured and plates were air dried for 1-2 h. Alcian blue stain was extracted from each well in 6N guanidine HCl with 0.25% Triton X-100 and the optical density (OD) was measured at 600 nm for each sample using a plate reader (Bjornsson, 1993).

Bioassay for AFC Proliferation

Similar to methods used to measure NPC proliferation, annulus fibrosus cell (AFC) proliferation in response to MPC CM was measured by EdU incorporation, with modifications to the culture periods found to be appropriate for AFCs. In brief, AFCs were seeded at 2,500 cells/cm$^2$ in serum-supplemented AFC growth medium. Following attachment overnight, cells were serum-starved for 48 h, prior to treatment with MPC CM for 3 days. In the last 18 h of culture, cells were pulsed with EdU. Cells were then harvested, stained and analysed by flow cytometry.

Bioassay for AFC Collagen Synthesis

To establish annulus fibrosus (AF) micromass cultures, annulus fibrosus cells (AFCs) were seeded in high density 2-dimensional (2D) cultures by adding a 10 µl drop of growth medium containing 100,000 cells to each well of a 48 well plate coated with human fibronectin at 5 µg/cm$^2$. Cells were allowed to adhere for 2 h followed by the addition of complete growth media to flood the well and overnight incubation of cells. On the following day, cells were washed once in warm PBS and serum-starved for 48 h prior to stimulation with MPC CM for 7 days. At the end of this culture period, MPC CM-stimulated collagen production was measured by hydroxyproline assay using a commercially available kit (Sigma, St Louis, Mo.). Media was aspirated and cells were washed with water. Deposited collagen was hydrolyzed in hydrochloric acid and the resultant supernatant was collected and evaporated. Each sample was incubated briefly in the presence of chloramine T to oxidize hydroxyproline. Finally, 4-(Dimethylamino)benzaldehyde was added to each sample, resulting in a colorimetric product that was read at 560 nm. In each experiment, a standard curve was set up using known amounts of hydroxyproline (0.2-1 µg), enabling quantitative determination of collagen synthesis in response to MPC CM treatment.

Isolation and Culture of Adult Human AFCs

Adult cadaveric disc tissues were obtained from donors screened for the following exclusion criteria:

TABLE 1

| Exclusion criteria for intervertebral tissue donors | |
|---|---|
| Age | <50 years old |
| Gender | No restrictions |
| Cause of death | Trauma with direct effects to the spine |
| | Cancer with musculoskeletal involvement |
| Disease History | Osteoarthritis |
| | Rheumatoid arthritis |
| | Other collagen/cartilage/bone diseases |
| Ambulation | Bedridden >1 month before death |

Tissue was immersed in preservation media consisting of DMEM-Ham's F12 (1:1)-10% fetal bovine serum (FBS) with antibiotics (e.g. penicillin (200 U/mL), streptomycin (200 mg/mL) and Fungizone (1.25 mg/mL) or Gentamicin (50 mg/mL)) at a final concentration of 0.1% (v/v) for transport to laboratory for digestion. To prepare tissues for digestion, AF tissue was carefully dissected from the NP tissue, which underwent separate digestion and isolation. Each disc was dissected and cultured separately. All digestions were conducted in 45 ml of a sterile DMEM-Hams F12-10% FBS as described previously (Melrose, Ghosh, Taylor, Latham, & Moore, 1997) (Melrose, Smith, Ghosh, & Taylor, 2001) (Shen, Melrose, Ghosh, & Taylor, 2003). In brief, tissues were finely diced with a scalpel under aseptic conditions. Approximately 2.5 g of diced tissue was transferred to a 50 ml conical tube containing an enzyme solution of 0.2% w/v Pronase and 0.01% w/v DNAase. Tissue was digested for 90 min at 37° C. Remaining tissue was washed with 10 ml PBS and the supernatant was discarded. Residual tissue was then digested with 0.05% w/v bacterial collagenase type 1A from *Clostridium histolyticum*, 0.01% w/v DNase (45 ml/tube) in DMEM-Hams F12-10% FBS containing antibiotics for several hours until tissue was completely disaggregated. Cells were collected by centrifugation (800 g×10 min) and washed once in DMEM-Hams F12-10% FBS. The resulting cell suspension was passed through a 70 µm cell strainer and re-suspended to determine cell count and viability. Both NPCs and AFCs were seeded in tissue culture treated flasks in DMEM-Hams F12-5% FBS and 2 mM L-glutamine. Primary NPCs and AFCs were cultured until 80-90% confluence, and shipped to Mesoblast laboratories in Houston. Primary cultures were harvested with 0.05% trypsin/0.1% EDTA and cryopreserved. Primary adult AFCs were thawed and seeded at 10,000 cells/cm$^2$ for 1 passage, then harvested to set-up bioassays.

Fetal AFCs were obtained from a commercial vendor (ScienCell, Carlsbad, Calif.).

Measurement of TGFβ1 Levels in MPC CM by ELISA

TGFβ1 levels in MPC CM were measured by ELISA according to the manufacturer's instructions (R&D Systems).

Prior to use, MPC CM was concentrated approximately 40-fold to facilitate the acid activation step required for the measurement of total TGFβ1 levels according to the manufacturer's protocol. Following acid treatment, the samples were reconstituted to the original volume in CBM for use in the bioassay.

The ELISA is performed following the manufacturer's protocol with modification to the diluent used for reconstitution and preparation of standards and sample dilution. The TGFβ1 standard provided in the kit is reconstituted in CBM supplemented with 0.5% BSA (CBM+0.5% BSA). Serial dilutions are prepared in CBM+0.5% BSA with final concentrations ranging from 31.2-2000 pg/ml. Samples are acid-activated and diluted 1:5 in CBM+0.5% BSA. Standards, samples and controls are added to a microplate pre-coated with a monoclonal antibody specific for TGFβ1. Following 2 h incubation at room temperature (RT), the plate is washed. TGFβ1 conjugate is added to each well and the plate is incubated for 2 h at RT. The plate is then washed again and substrate solution is added to each well and incubated for 30 min at RT. Stop solution is added to each well and the optical density (OD) of each sample is read on a microplate reader set to 450 nm with wavelength correction at 570 nm. A standard curve is constructed using a four parameter logistic curve fit. The concentration of TGFβ1 in each sample is derived from the standard curve and corrected for dilutions to obtain a final result.

Generation of TGFβ1 knock-down MPC

Freshly thawed MPC products (n=4) were transfected with TGFβ1 siRNA or scrambled oligonucleotide as control. Cells were suspended in serum-free αMEM and combined with a transfection mixture containing TGFβ1 siRNA or scrambled siRNA (500 pmol, Life Technologies, Carlsbad, Calif.) and Lipofectamine (Life Technologies). Cells were then seeded at high density onto fibronectin-coated plates and allowed to attach overnight. The following day, cells were washed and medium was replaced with CBM+0.5% BSA. Cells were returned to the incubator and left undisturbed at 37° C., 5% $O_2$/95% $CO_2$ for 72 h. At the end of this culture period, culture supernatant was collected, centrifuged to pellet cells or debris in suspension, then aliquotted and stored at −80° C. until assay.

Example 2 Proof of Concept Experiments

A series of in vitro studies were undertaken to model and evaluate the potential mechanisms by which MPCs may mediate therapeutic benefit in degenerative disc disease (DDD), with a view to establishing appropriate potency assays for MPCs in disc repair.

Under laboratory conditions, MPCs possess multilineage potentiality, including the capacity for in vitro chondrogenic differentiation in response to appropriate inductive cues. The classic in vitro chondrogenesis assay involves culturing cells in high density pellets in the presence of TGFβ1 over a period of 3 weeks (Johnstone, Hering, Caplan, Goldberg, & Yoo, 1998). The pellet is then fixed, sectioned and stained to detect the presence of proteoglycans, a hallmark of chondrocyte activity. Given the time required to perform this assay and the non-quantitative methods for assessment, this assay was considered not amenable to qualification and validation as a release assay. Therefore, development of an in vitro chondrogenic release assay was not pursued. Instead, efforts were focussed on identifying paracrine mechanisms of action of MPCs on intervertebral disc (IVD) cells as a basis for potency assay development.

MPCs secrete a diverse range of bioactive soluble factors, including factors known to attenuate inflammation, promote cellular proliferation and stimulate matrix production (See, et al., 2011). The cytokine profile of multiple lots of MPC product was examined and secretion of a broad range of bioactive molecules confirmed. Based on these data, it was hypothesized that following introduction into the IVD, MPCs may stimulate endogenous repair processes by paracrine mechanisms through the release of soluble molecules that act on disc-resident cells. The present inventors focussed on the identification of secreted factors that may contribute to the survival, proliferation and differentiation of NPCs and/or AFCs, leading to sustained enhancement of disc function. An extensive screen of the relevant literature was conducted to identify secreted factors with anabolic effects on disc cells. Factors identified by this survey were subsequently screened for in MPC CM by means of immunoassays and from these data, TGFβ1 was identified as the lead candidate.

To determine whether TGFβ1-mediated mechanisms of action may provide a foundation for development of a potency assay for assessment of MPC product, in vitro proof-of-concept experiments were performed with the following aims:
1. To determine whether MPC CM stimulates NPC proliferation and matrix production; and
2. To determine whether MPC CM stimulates AFC proliferation and matrix production; and
3. To determine whether TGFβ1 in MPC CM mediates the in vitro bioactivity of MPC CM on disc cells.

MPC-Derived Soluble Factors Stimulate NPC Proliferation and Proteoglycan Production The NP is primarily composed of the proteoglycan, aggrecan, a water-binding molecule that provides the substrate for swelling pressure within the IVD. NPCs are the primary source of proteoglycans in the IVD, and thereby play a key role in maintaining tissue structure and function. In addition, deposition of proteoglycans by NPCs may be important in preserving the aneural environment of the healthy, pain-free disc, since in vitro studies have shown that an intact proteoglycan matrix repels neurite ingrowth (Johnson, Caterson, Eisenstein, Hynds, Show, & Roberts, 2002). Conversely, DDD is associated with NPC death, matrix disruption and loss and neurite ingrowth (Loreto, Musumeci, Castorina, Loreto, & Martinez, 2011) (Melrose, Roberts, Smith, Menage, & Ghosh, 2002). Therefore, repair of damaged NP tissue may require both maintenance of the resident NPC population and stimulation of matrix synthesis. In turn, support of NPCs may improve disc structure and function and attenuate pain sensation. To examine whether MPC CM has an impact on NPC function, bioassays were established to measure the effects of MPC CM on human NPC proliferation and proteoglycan production in vitro.

Figure 2:
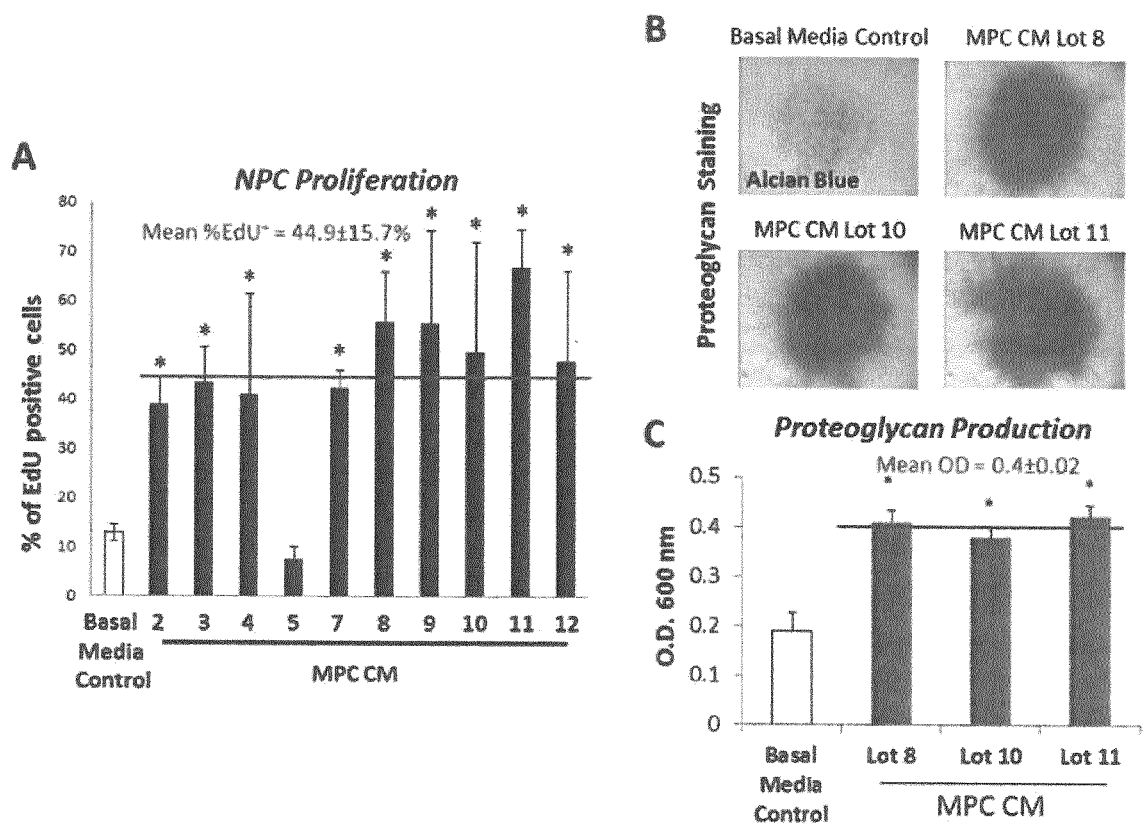
FIG. 2: Effects of MPC CM on proliferation and matrix composition of human NPCs in micromass cultures. (A) Data showing EdU incorporation in nucleus pulposus cell (NPC) proliferation in response to mesenchymal precursor cell (MPC) conditioned media (CM). Data is expressed as Mean±SD of % positive EdU incorporation. n=3 replicates/condition. (B) Representative images of Alcian Blue staining for sulfated GAG proteoglycans in human NPC micromass cultures. (C) Semi-quantification of proteoglycans extracted from NP micromass cultures. Data is expressed as Mean±SD. n=3 replicates/condition. Significance assigned to p≤0.05 vs basal medium control.

Samples of CM from various lots of MPCs were tested for activity in the NPC proliferation assay, as determined by EdU incorporation. In FIG. 2A, nine out of the ten lots tested stimulated a significant increase in the proportion of actively dividing NPCs in culture (mean % EdU$^+$ cells=44.9±15.7%, range=38.9-66.9%, n=10 lots from 4 donors) compared to unstimulated control cells (12.9%). The remaining lot had no significant effect on NPC proliferation compared with basal medium control.

In 2D high density culture, NPCs constitutively produced low levels of proteoglycans, identified by Alcian blue staining (FIG. 2B). CM from three different lots of MPCs significantly enhanced proteoglycan synthesis above these baseline levels, as indicated by more intense Alcian blue staining relative to unstimulated control cells. To quantitate proteoglycan synthesis, Alcian blue stain was extracted for absorbance readings. MPC CM-treatment of NPCs resulted in an approximately 2-fold increase in proteoglycan content (mean OD=0.40±0.02, range=0.38-0.42, n=3 lots from 1 donor) above that in control cells grown in basal medium (FIG. 2C).

Together, these data provide evidence that MPC CM contains factor(s) with anabolic effects on NPCs as measured by effects on proliferation and synthesis of proteoglycans. Therefore, MPC treatment may stimulate reparative mechanisms in the injured disc via paracrine actions on NPCs.

MPC-Derived Soluble Factors Stimulate AFC Proliferation and Collagen Synthesis

The AF of IVD is primarily composed of fibrillar collagen I and collagen II, which form lamellar sheets that surround the NP. Levels of collagen I are high in the outer layers and diminish towards the interface with the NP, while collagen II content increases from the outer layers and is highly enriched toward the center of the tissue. These collagen gradients provide both tensile strength and elasticity to the disc, which support IVD structure and function. The intact AF plays an important role in creating a barrier against neuronal and vascular ingrowth into disc tissue. In contrast, breaches in the AF, as occur in DDD, lead to structural and functional impairment of the IVD and pain associated with vascular and neuronal invasion. The collagen matrix of the AF is maintained by resident AFCs. AFCs from degenerative discs have been shown to exhibit an impaired phenotype, characterized by down-regulation of genes related to ECM components and cellular proliferation (Gruber, Hoelscher, & Hanley, 2010). The AF population in DDD tissue has been shown to contain an increased proportion of senescent cells and a concomitant reduction in the proportion of proliferating cells (Gruber, Ingram, Davis, & Hanley, 2009). Therapeutic strategies that help maintain the pool and activity of AFCs may lead to long term benefit by restoration of AF structure and function. To determine whether MPC-derived factors have an impact on AFC function, bioassays were established to measure the effects of MPC CM on human AFC proliferation and collagen synthesis in vitro.

Figure 3:
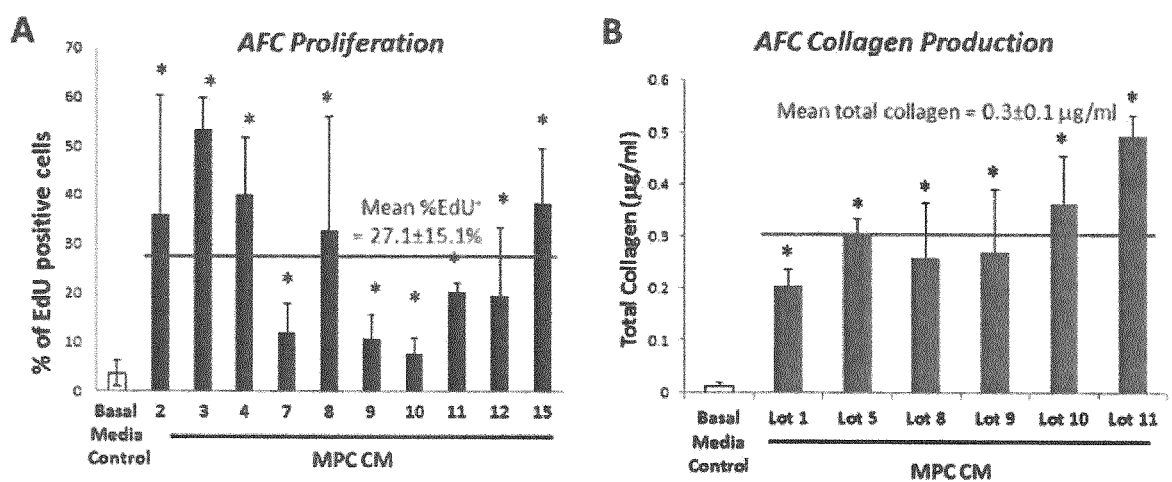
FIG. 3: In vitro effects of MPC CM on proliferation and matrix production of human AFC in micromass cultures. (A) Data showing annulus fibrosus cell (AFC) proliferation in response to MPC CM. Data is expressed as Mean±SD of % positive EDU incorporation. n=3 replicates/condition. (B) Quantification of total collagen produced by AF micromass cultures in response to MPC CM. Representative data from one donor expressed as Mean±SD. n=3 replicates/condition. Significance assigned to p≤0.05 vs basal medium control.

FIG. 3A shows that CM samples generated from different lots of MPCs increased AFC proliferation, measured by EdU incorporation, above levels observed in cells grown in basal medium alone. In this experiment, CM from all seven lots tested stimulated a significant increase in the proportion of actively dividing cells in culture (mean % EdU$^+$ cells=27.1±15.1%, range=7.8-53.2%, n=10 lots from 3 donors) compared with control medium (3.6%).

In addition to stimulating AFC proliferation, MPC CM increased AFC collagen synthesis. AFCs treated with MPC CM contained significantly higher levels of hydroxyproline (mean hydroxyproline content=0.3±0.1 μg/ml, range=0.2-0.5 g/ml, n=6 lots of MPCs from 3 donors) compared with cells grown in basal medium alone (0.01 μg/ml) (FIG. 3B). Despite the observed variability inherent in these types of bioassays, together, these data clearly demonstrate that MPC CM contains soluble factors that stimulate AFC activity.

Role of TGFβ1 in AFC collagen synthesis

To investigate the potential contribution of TGFβ1, the levels of TGFβ1 in CM derived from multiple MPC product lots encompassing five different donors was surveyed. The putative causal role of TGFβ1 on AFC collagen synthesis in vitro in the presence and absence of a neutralizing anti-TGFβ1 antibody was subsequently examined.

Figure 4:
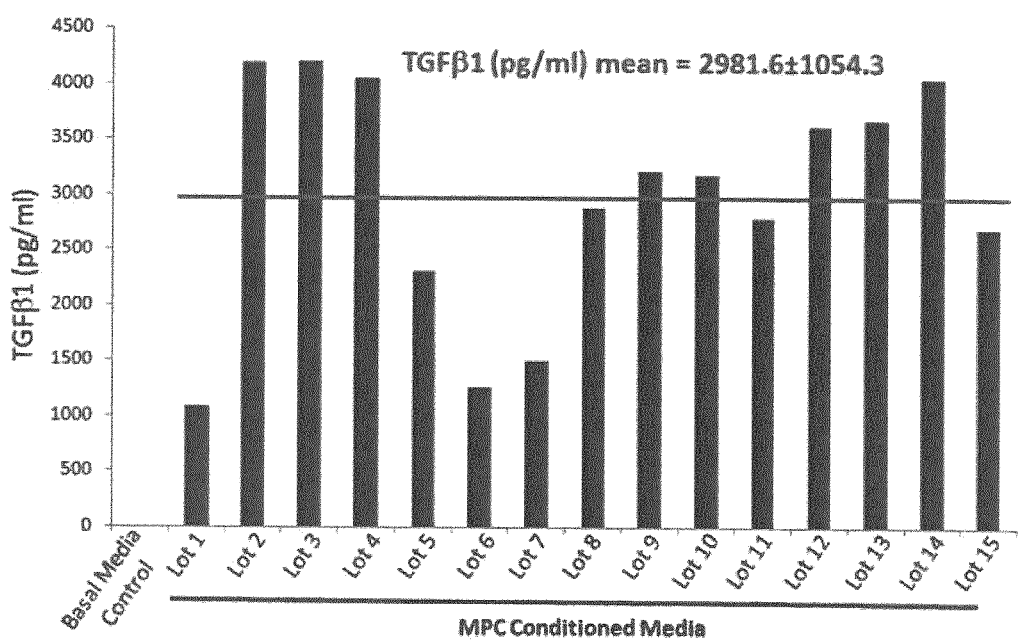
FIG. 4: Levels of TGFβ1 detected in MPC CM. Detection of TGFβ1 in MPC CM measured by ELISA. Data is expressed as average of duplicate samples. n=15 lots of MPCs derived from 5 different donors.

TGFβ1 levels in MPC CM were measured by ELISA according to the manufacturer's instructions (R&D Systems, Minneapolis, Minn.). Levels of TGFβ1 in MPC CM ranged from 1083.1-4202.8 pg/ml (mean=2981.6±1054.3 pg/ml, n=15 lots generated from 5 different donors) (FIG. 4).

Figure 5:
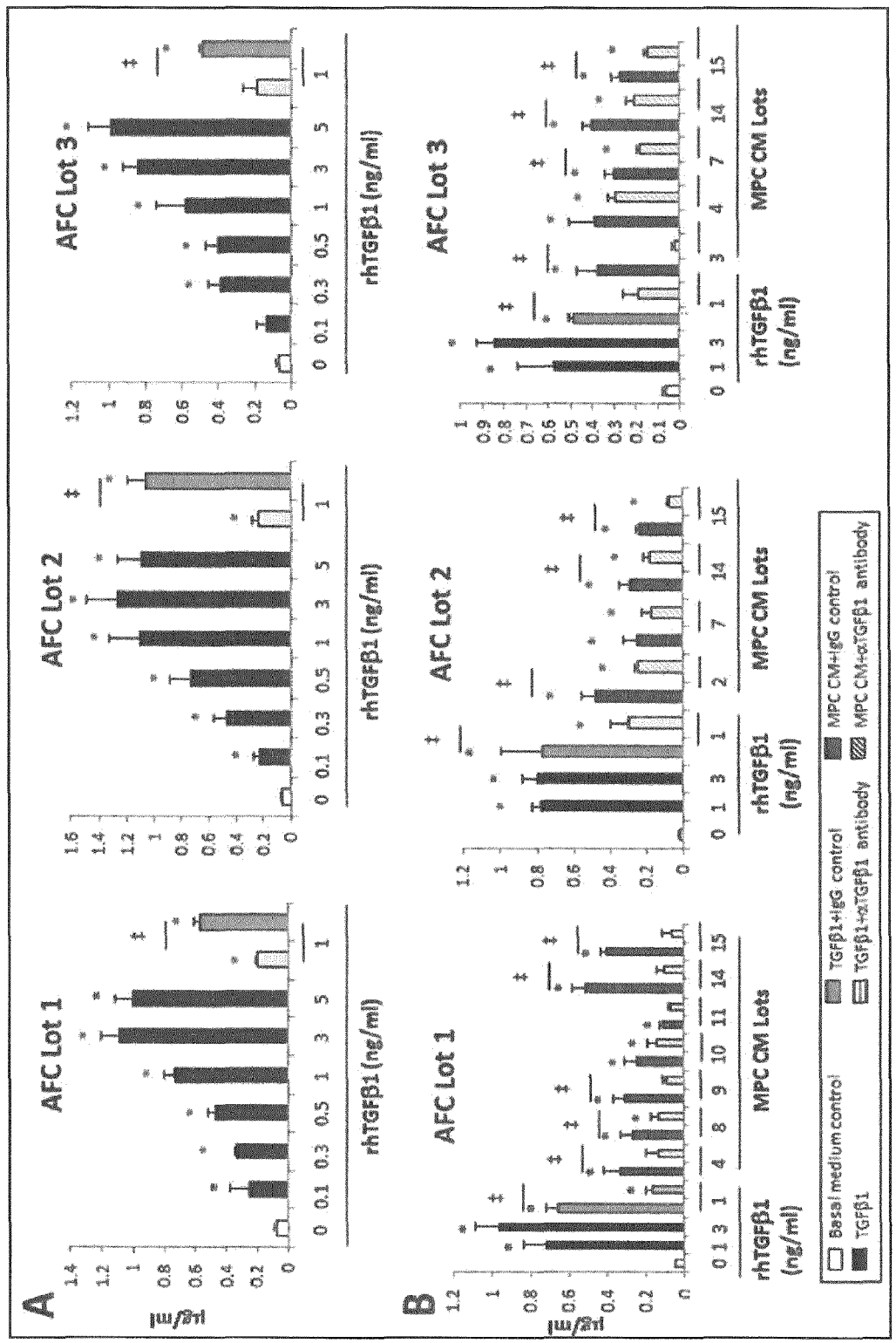
FIG. 5: Effects of TGFβ1 and MPC CM on hydroxyproline content in micromass cultures of human AFCs. (A) Dose response to recombinant human TGFβ1 (rhTGFβ1) mediated collagen production in AF micromass cultures from 3 AFC donors. Data demonstrate significant inhibition of rhTGF 1 response with anti-TGFβ1 neutralizing antibody. (B) Quantification of total collagen produced by AF micromass cultures in response to MPC CM following anti-TGFβ1 neutralization or IgG control. Data generated from 3 AFC donors and 4-7 lots of MPC CM. Data are expressed as Mean±SD. n=3 replicates/condition. Significance assigned to p≤0.05; * vs basal medium control; ‡vs IgG control.

The data confirmed that MPC reproducibly secrete robust levels of TGFβ1 in their CM. As shown in FIG. 5A, three different lots of AFCs demonstrated a clear TGFβ1 dose-dependent synthesis of collagen, plateauing between 1-3 ng/ml TGFβ1. In the presence of a neutralizing anti-TGFβ1 antibody, collagen synthesis by AFCs in response to 1 ng/ml TGFβ1 was reduced to levels marginally above those obtained in the absence of TGFβ1. These data validate the linear dose-responsiveness of the target AFC population to TGFβ1 and the potency of the anti-TGFβ1 neutralizing antibody.

To examine whether MPC-derived TGFβ1 plays a causative effect in AFC collagen production, MPC CM samples were pre-treated with a neutralizing antibody against TGFβ1, prior to addition to AF cultures. In FIG. 5B, left panel, CM from 7 MPC lots each stimulated a statistically significant increase in hydroxyproline content in AFCs compared to basal medium control. Neutralization of TGFβ1 activity resulted in significant reductions in hydroxyproline content in 5 out of 7 lots. Trends towards decreased collagen synthesis were seen in the remaining 2 lots, which also contained the lowest levels of activity in this assay. CM samples were tested across different lots of AFCs from different donors (FIG. 5B, center and right panels) and a similar pattern of results was observed in each experiment. Complete inhibition of collagen synthesis in the presence of an anti-TGFβ1 neutralizing antibody (compared to the equivalent level of control antibody) was demonstrated in several lots of CM, thereby demonstrating that in these specific instances, TGFβ1 is the sole causative factor in promoting collagen synthesis.

Conclusions from Proof of Concept Experiments

The data demonstrates that MPC CM contains soluble factors that stimulate NPC and AFC proliferation and matrix production. TGFβ1, which has been shown to have anabolic effects on disc cells, was detected in CM from multiple MPC lots. Moreover, TGFβ1 was shown to be a key effector of collagen synthesis in cells treated with MPC CM. The data suggests that MPC-derived TGFβ1 stimulates AFC collagen synthesis and may thereby contribute to repair of the AF and long term therapeutic benefit in the context of DDD. Therefore, detection of TGFβ1 levels in MPC CM represents a potential surrogate measure of MPC potency for disc repair.

The data also demonstrates establishment of quantitative assays to measure TGFβ1-driven bioactivity, namely the EdU incorporation assay as a measure of NPC and AFC proliferation and the hydroxyproline assay as a measure of AFC collagen synthesis. The hydroxyproline assay was performed using different lots of AFCs and the findings support the reproducibility of the collagen synthesis-promoting actions of MPC CM on AFCs, and the contribution of TGFβ1 to this effect, independent of target cell donor. Similar efforts to compare the performance of different NP and AFC lots have been undertaken in assessment of the EdU incorporation assay. Some variability in TGFβ1 levels between MPC product lots was observed (range in lots screened=1083.1-4202.8 pg/ml). Importantly, this range of TGFβ1 levels was shown to have measurable activity, that was statistically significant above baseline control, in the AFC collagen synthesis assays using recombinant human TGFβ1 (rhTGFβ1). Together, these data support the use of this bioassay to measure TGFβ1 bioactivity in MPC CM.

Example 3 Comparability of Fetal AFCs and Adult AFCs

A bioassay to measure the effects of MPC CM on AFC collagen synthesis was previously developed. The assay was developed using fetal AFCs, due to their commercial availability. This factor represents an important supply benefit in potency assay development efforts. In contrast, adult AFCs are presently not commercially available. The present inventors sought to verify that fetal AFCs are a suitable alternative to adult AFCs in the collagen synthesis bioassay. Therefore, they compared the effects of rhTGFβ1 and MPC CM on micromass cultures of fetal AFCs and adult AFCs.

Figure 6:
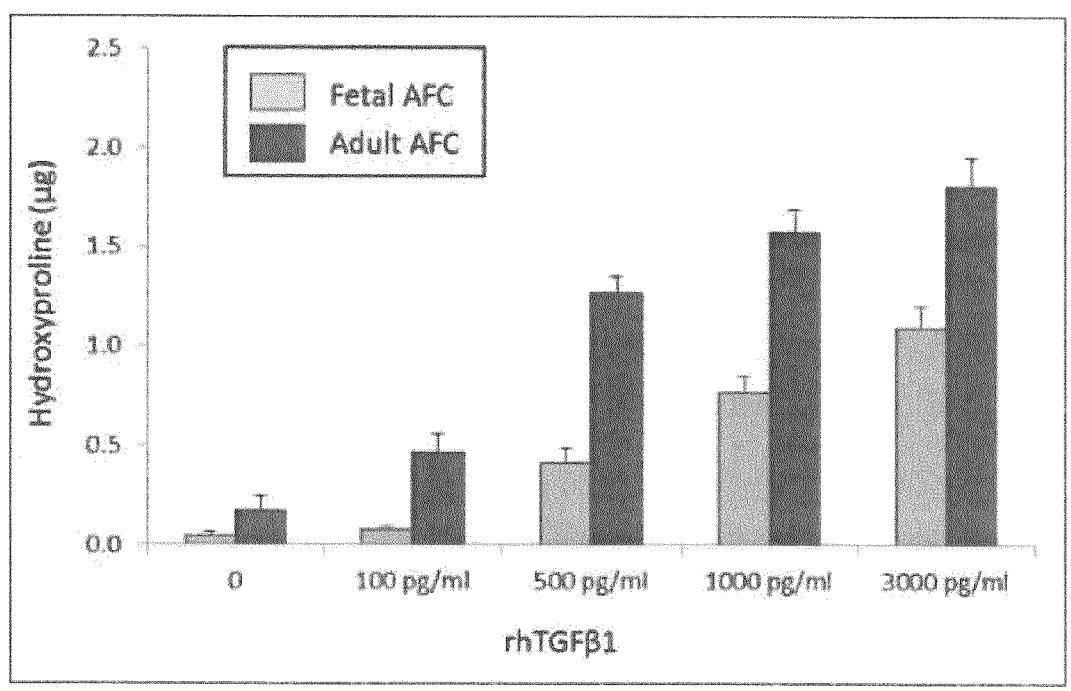
FIG. 6: Effects of rhTGFβ1 on hydroxyproline content in fetal vs adult human AFC micromass cultures. Collagen production in response to rhTGFβ1 by fetal and adult AFC micromass cultures. Each data point represents 3 fetal or adult AFC donors. Data are expressed as Mean±SD. n=6-9 replicates/condition.

Similar to fetal cells, adult AFCs demonstrated a dose-dependent response to rhTGFβ1 (0.1-3 ng/ml) (FIG. 6 and Table 2). In comparison to fetal cells, baseline levels of collagen were higher in cultures of adult AFCs, and the magnitude of response to low levels of TGFβ1 (100 pg/ml) was also greater (FIG. 6 and Table 2). Production in response to 500 pg/ml was similar between fetal AFCs and adult AFCs. While the dose-response curve at 1-3 pg/ml TGFβ1 began to plateau in adult AFC cultures, the curve remained linear for fetal AFCs.

Figure 7:
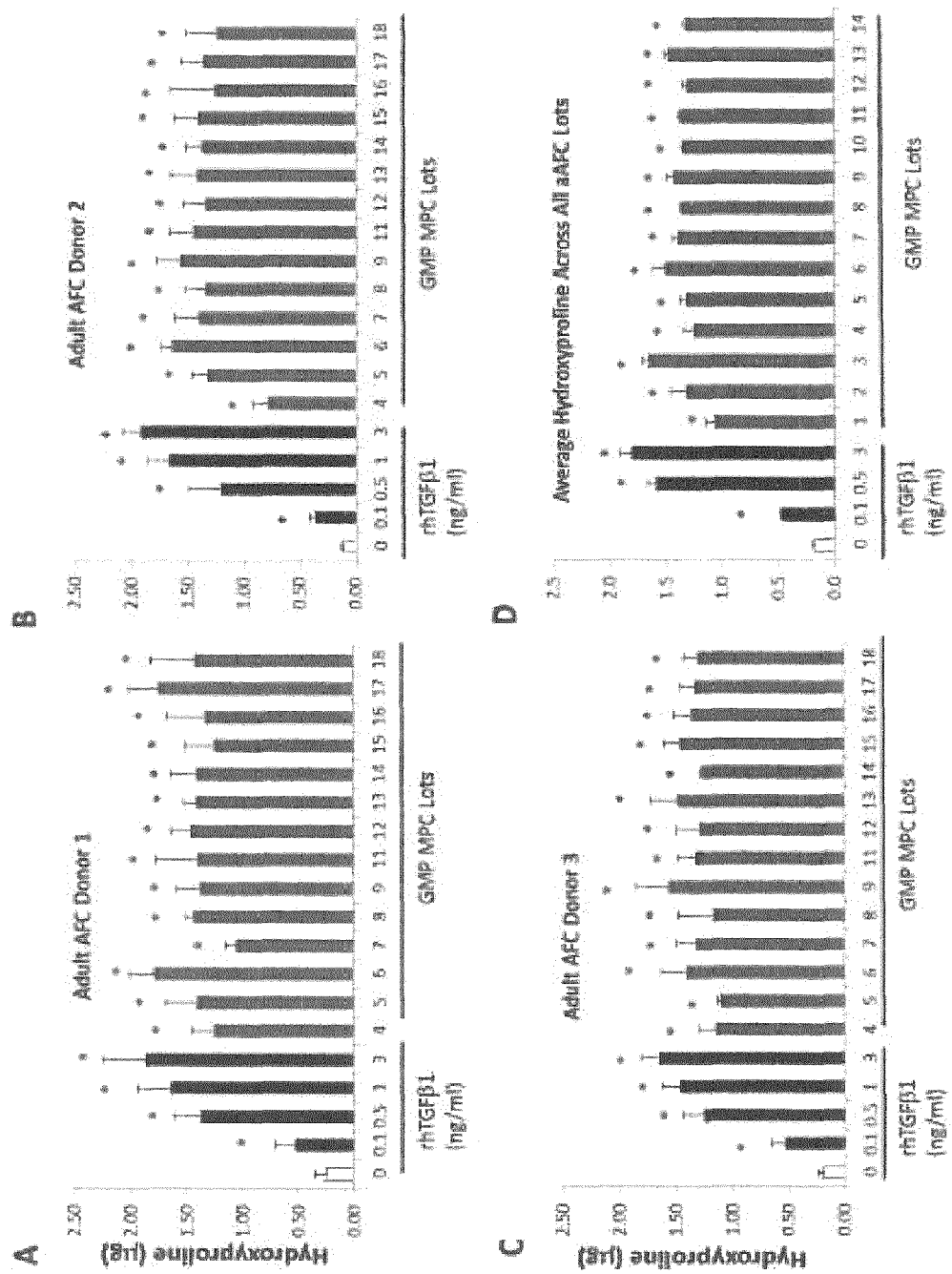
FIG. 7: Effects of TGFβ and MPC CM on hydroxyproline content in adult human AFC micromass cultures. Collagen production in response to rhTGFβ1 or MPC CM by adult AFC micromass cultures from 3 AFC donors (A, B, C). Data are expressed as Mean±SD. n=3-8 replicates/condition. (D) Mean hydroxyproline content in the 3 adult AFC lots. Significance assigned to p≤0.05 (relative to basal medium control (0 ng/ml rhTGFβ1)).

Treatment of adult AFCs with MPC CM stimulated robust and significant increases in collagen production in adult AFCs (FIG. 7 and Table 3).

TABLE 2

Response of fetal and adult AFCs to TGFβ1 stimulation

| rh TGFβ1 (pg/ml) | Fetal AFC - Lot 5945 | | | Fetal AFC - Lot 4755 | | | Fetal AFC - Lot 4729 | | | All fAFC | |
|---|---|---|---|---|---|---|---|---|---|---|---|
| | Average Hydroxyproline ($\mu g/10^5$ cells) | SD | N | Average Hydroxyproline ($\mu g/10^5$ cells) | SD | N | Average Hydroxyproline ($\mu g/10^5$ cells) | SD | N | Average Hydroxyproline ($\mu g/10^5$ cells) | SD |
| 0 | 0.069 | 0.052 | 9 | 0.034 | 0.022 | 8 | 0.038 | 0.011 | 9 | 0.047 | 0.019 |
| 100 | 0.100 | 0.033 | 9 | 0.080 | 0.035 | 9 | 0.072 | 0.014 | 9 | 0.084 | 0.015 |
| 500 | 0.453 | 0.075 | 9 | 0.466 | 0.113 | 9 | 0.327 | 0.165 | 9 | 0.415 | 0.077 |
| 1000 | 0.714 | 0.134 | 9 | 0.725 | 0.265 | 9 | 0.862 | 0.135 | 6 | 0.767 | 0.082 |
| 3000 | 1.187 | 0.205 | 9 | 0.979 | 0.205 | 9 | 1.121 | 0.058 | 6 | 1.096 | 0.106 |

| rh TGFβ1 (pg/ml) | Adult AFC - Donor 1 | | | Adult AFC - Donor 2 | | | Adult AFC - Donor 3 | | | All aAFC | |
|---|---|---|---|---|---|---|---|---|---|---|---|
| | Average Hydroxyproline ($\mu g/10^5$ cells) | SD | N | Average Hydroxyproline ($\mu g/10^5$ cells) | SD | N | Average Hydroxyproline ($\mu g/10^5$ cells) | SD | N | Average Hydroxyproline ($\mu g/10^5$ cells) | SD |
| 0 | 0.245 | 0.101 | 6 | 0.105 | 0.022 | 9 | 0.185 | 0.043 | 9 | 0.179 | 0.070 |
| 100 | 0.523 | 0.183 | 6 | 0.359 | 0.058 | 9 | 0.524 | 0.127 | 9 | 0.469 | 0.095 |
| 500 | 1.366 | 0.237 | 7 | 1.198 | 0.294 | 9 | 1.247 | 0.183 | 8 | 1.270 | 0.086 |
| 1000 | 1.633 | 0.292 | 9 | 1.655 | 0.197 | 9 | 1.451 | 0.168 | 9 | 1.580 | 0.112 |
| 3600 | 1.861 | 0.382 | 9 | 1.910 | 0.168 | 9 | 1.638 | 0.164 | 9 | 1.803 | 0.145 |

TABLE 3

Conditioned medium samples generated from MPC lots tested in adult AFCs

| | | Adult AFC | | | | | | | | | | | |
|---|---|---|---|---|---|---|---|---|---|---|---|---|---|
| | | Donor 1 | | | Donor 2 | | | Donor 3 | | | All aAFC | | |
| Arbitrary Lot # | TGFβ1 (pg/ml) | Average Hydroxy-proline (μg) | SD | N | Average Hydroxy-rpoline (μg) | SD | N | Average Hydroxy-rpoline (μg) | SD | N | Average Hydroxy-rpoline (μg) | SD | N |
| GMP-4 | 3084.53 | 1.253 | 0.188 | 5.000 | 0.779 | 0.138 | 5.000 | 1.141 | 0.157 | 6.000 | 1.063 | 0.253 | 16.00 |
| GMP-5 | 3191.16 | 1.405 | 0.276 | 6.000 | 1.322 | 0.144 | 6.000 | 1.102 | 0.030 | 3.000 | 1.311 | 0.219 | 15.00 |
| GMP-6 | 3601.95 | 1.783 | 0.218 | 6.000 | 1.636 | 0.099 | 3.000 | 1.393 | 0.231 | 3.000 | 1.649 | 0.246 | 12.00 |
| GMP-7 | 2569.11 | 1.046 | 0.101 | 6.000 | 1.399 | 0.218 | 6.000 | 1.308 | 0.179 | 6.000 | 1.251 | 0.224 | 18.00 |
| GMP-8 | 3178.29 | 1.429 | 0.077 | 6.000 | 1.334 | 0.180 | 3.000 | 1.160 | 0.323 | 5.000 | 1.313 | 0.234 | 14.00 |
| GMP-9 | 3480.65 | 1.371 | 0.216 | 6.000 | 1.562 | 0.211 | 8.000 | 1.552 | 0.291 | 4.000 | 1.496 | 0.235 | 18.00 |
| GMP-11 | 3089.14 | 1.394 | 0.385 | 5.000 | 1.450 | 0.205 | 6.000 | 1.317 | 0.164 | 6.000 | 1.387 | 0.249 | 17.00 |
| GMP-12 | 3620.38 | 1.452 | 0.191 | 6.000 | 1.340 | 0.201 | 5.000 | 1.276 | 0.209 | 6.000 | 1.357 | 0.203 | 17.00 |
| GMP-13 | 3537.31 | 1.404 | 0.119 | 6.000 | 1.416 | 0.237 | 6.000 | 1.470 | 0.246 | 8.000 | 1.434 | 0.204 | 20.00 |
| GWP-14 | 1979.12 | 1.404 | 0.230 | 6.000 | 1.370 | 0.153 | 6.600 | 1.254 | 0.025 | 6.000 | 1.343 | 0.164 | 18.00 |
| GMP-15 | 3119.66 | 1.240 | 0.275 | 6.000 | 1.405 | 0.218 | 6.000 | 1.445 | 0.156 | 6.000 | 1.363 | 0.227 | 18.00 |
| GMP-16 | 2963.90 | 1.323 | 0.354 | 5.000 | 1.255 | 0.393 | 4.000 | 1.341 | 0.174 | 3.000 | 1.305 | 0.307 | 12.00 |
| GMP-17 | 3770.39 | 1.746 | 0.262 | 6.000 | 1.365 | 0.193 | 6.000 | 1.316 | 0.133 | 6.000 | 1.476 | 0.274 | 18.00 |
| GMP-18 | 2942.00 | 1.417 | 0.402 | 6.000 | 1.231 | 0.285 | 6.000 | 1.286 | 0.133 | 6.000 | 1.311 | 0.288 | 18.00 |
| All Lot Mean | 3151.97 | 1.405 | | | 1.347 | | | 1.311 | | | 1.361 | | |
| All Lot SD | 469.65 | 0.186 | | | 0.195724344 | | | 0.127 | | | 0.134 | | |
| All Lots CV | 0.1490 | 0.1324 | | | 0.1453 | | | 0.0968 | | | 0.0981 | | |
| Min | 1979.12 | 1.05 | | | 0.78 | | | 1.10 | | | 1.06 | | |
| Max | 377039 | 1.78 | | | 1.64 | | | 1.55 | | | 1.65 | | |

Together, these data demonstrate that stimulation of micromass cultures of fetal and adult AFCs with TGFβ1 increases collagen production in a dose-dependent manner. Treatment of adult AFCs with MPC CM resulted in robust increases in hydroxyproline content, similar to the effects observed previously in fetal AFCs. Together, these data indicate that fetal AFCs represent a suitable alternative to adult AFCs for assessing the effects of MPC CM on collagen production in this cell type.

Example 4 TGFβ1 Potency Assay Development for MPC Product for DDD

In vitro models were used to examine a number of potential paracrine mechanisms by which MPCs may have beneficial effects in DDD (Example 2). Among these, stimulation of collagen production by AFCs may represent an important step toward long term therapeutic benefit. Augmentation of AFC collagen production may result in repair of the structural integrity of the disc and inhibit vascular and neuronal ingrowth, and in turn improve the biomechanical function of the disc and reduce pain.

To examine the effects of MPC-derived soluble factors on AFC collagen production, the present inventors developed a quantitative assay to measure levels of hydroxyproline (a major component of collagen) in micromass cultures of AFCs (Example 2). The assay was established using 3 different lots of fetal AFCs and rhTGFβ1. The present inventors showed that rhTGFβ1 (across a concentration range of 100-3000 pg/ml) dose-dependently stimulated collagen production in AFCs (FIG. 5A). The present inventors also demonstrated that MPC CM stimulates collagen production in this bioassay. The collagen-stimulating effects of MPC CM were attributable, at least in part, to TGFβ1 activity, since an anti-TGFβ1 neutralizing antibody abrogated these effects (FIG. 5B). Importantly, the collagen-stimulating effects of both rhTGFβ1 and MPC CM were reproducible across multiple lots of AFCs representing different donors, indicating that these effects were independent of AFC donor. The present inventors also confirmed that commercially-available fetal AFCs are a suitable alternative to adult AFCs in this bioassay (Example 3). Together, these data provide two key elements to potency assay development: firstly, the data provide proof of concept that MPCs may stimulate collagen production by AFCs through paracrine mechanisms and that TGFβ1 plays a key role in this setting. Secondly, the data supports the utility of the AFC collagen synthesis assay to measure MPC CM bioactivity. Thus, given the robust levels of TGFβ1 found in MPC CM and the causative role of TGF 1 in the effects of MPC CM on AFC collagen production, the data also suggest that TGFβ1 is a rational candidate surrogate marker of MPC bioactivity that is relevant in DDD.

An enzyme-linked immunosorbent assay (ELISA)-based method was employed to detect TGFβ1 in MPC CM as a potency assay for MPCs for DDD.

Figure 8:
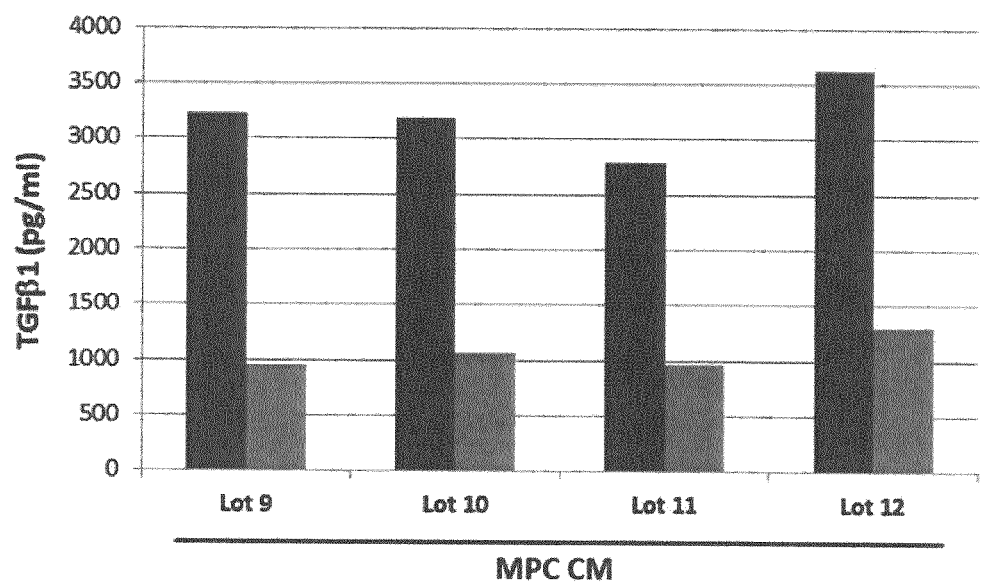
FIG. 8: TGFβ1 levels in CM from MPCs grown in different basal media. Detection of TGFβ1 in MPC CM measured by ELISA following growth in optimal vs suboptimal media formulations for CM generation. Dark bars=Chondrogenic Basal Medium+0.5% Bovine Serum Albumin (CBM+0.5% BSA). Light bars=EBM-2+0.5% BSA). Data is expressed as average of duplicate samples. All MPC lots derived from a single donor.

TGFβ1 levels were measured in CM from MPCs grown in two different basal media using a commercially available ELISA. The data show a marked difference in TGFβ1 levels in CM as a function of media formulation (FIG. 8). These samples were produced in experiments to determine the optimal basal medium for generation of CM for assessment of MPC TGFβ1 production and in vitro bioactivity. CBM supplemented only with 0.5% BSA (FIG. 8, dark bars) was selected for use in these experiments and reflects a medium that balances support of MPC function and compatibility with downstream application in IVD-based functional bioassays. By extension, these data also demonstrate that the TGFβ1 ELISA may be used to detect changes in manufacturing processes that may adversely affect TGFβ1 synthesis by MPC.

MPC CM Stimulate Collagen Production by Human AFCs and Contains Robust Levels of TGFβ1

FIG. 7 and Table 4 show the effects of MPC CM on collagen production in 3 independent lots of fetal AFCs. The data demonstrate that each AFC lot responded in a dose-dependent manner to rhTGFβ1 (100-3000 pg/ml), which was included in experiments to confirm system suitability. CM from GMP lots 1-18 were each assayed on AFC lot 4729 (FIG. 7A). Where aliquots were available, CM samples were also assayed on AFC lots 5945 and 4755 (FIG. 7B and FIG. 7C). Each MPC lot stimulated a statistically significant increase in collagen production over unstimulated controls in AFC lot 4729 (FIG. 7A). This effect was reproduced in AFC lots 5945 and 4755 (FIG. 7B and FIG. 7C). FIG. 7D shows the average responses of all AFC lots to each MPC CM sample.

Figure 9:
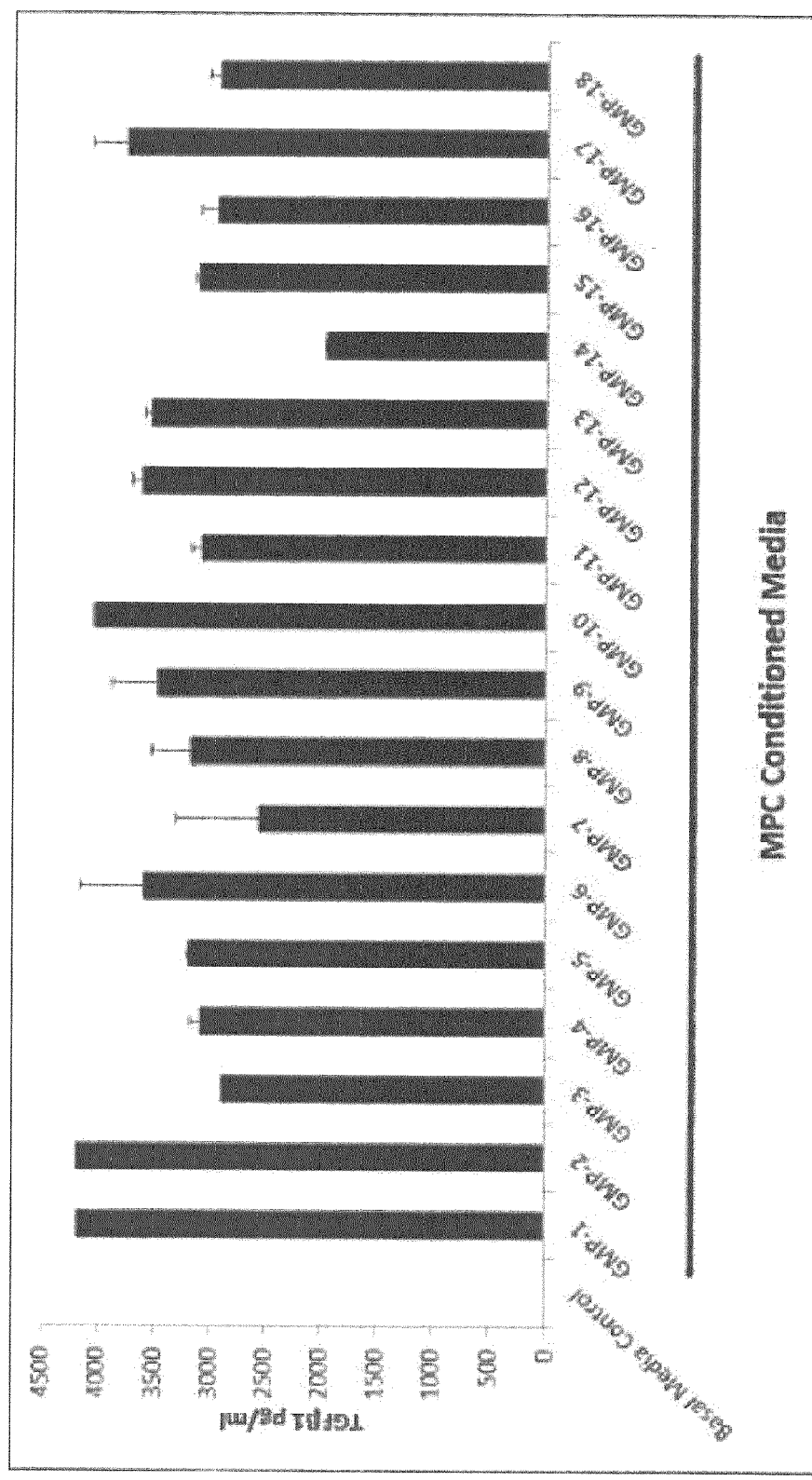
FIG. 9: Levels of TGFβ1 detected in MPC CM. Detection of TGFβ1 required acid-treatment of samples and measurements therefore reflect total TGFβ1 in CM. Data is expressed as Mean±SD. n=18 lots of MPCs derived from 4 different donors.

The collagen-stimulating activity of MPC CM was associated with the presence of robust levels of TGFβ1 in each sample (FIG. 9 and Table 4). Under standardized culture conditions, total TGFβ1 levels in MPC supernatants ranged from 1979.12-4202.82 pg/ml, with a mean of 3303.16±569.56 pg/ml.

Establishing a Minimum Threshold Effect of MPC CM in the AFC Collagen Synthesis Bioassay In order to establish a preliminary release specification for MPCs based on TGFβ1 secretion, the present inventors first sought to identify a minimum threshold effect of MPC CM in the AFC collagen synthesis bioassay. The present inventors reasoned that this threshold would be a function both of the characteristics of the sample type (CM), and of the bioassay itself. As shown in FIG. 7 and FIG. 9, MPC CM samples from the lots tested contain a range of TGFβ1 levels (1979.12-4202.82 pg/ml), all of which resulted in significant increases in collagen synthesis above unstimulated baseline control. In addition, the present inventors noted that although the average level of TGFβ1 in MPC CM samples was 3303.16±569.56 pg/ml, the effect of MPC CM on collagen production was less than that elicited by rhTGFβ1 alone at 3000 pg/ml, consistent with the hypothesis that MPC CM may contain factors that inhibit the actions of TGFβ1 in this assay. Therefore, in order to establish the level of bioactivity in MPC CM that would reflect sub-potent activity in this bioassay, the present inventors generated CM from MPC lots in which TGFβ was reduced using siRNA technology.

Characterization of CM from TGFβ1 knockdown MPCs

The present inventors verified TGFβ1 knockdown by measuring TGFβ1 levels in MPC CM by ELISA. FIG. 10A and Table 5 show TGFβ1 levels in CM from each MPC lot transfected with control scrambled oligonucleotide or TGFβ1 siRNA. Transfection of MPCs with 500 pmol siRNA resulted in approximately 90% reductions in TGFβ1 levels compared to scrambled controls, without direct effect on viability (data not shown).

Having confirmed knockdown of TGFβ1, MPC CM samples were tested in the AFC hydroxyproline assay. FIG. 10B and Table 5 show that CM from MPCs transfected with scrambled siRNA stimulated a similar level of collagen production in AFC as the average level stimulated by all MPC lots tested. In contrast, AFC collagen synthesis in response to TGFβ1 knockdown MPC CM was significantly reduced compared to AFC stimulated with MPC CM from scrambled siRNA controls. However, the effect of CM from TGFβ1 knockdown MPCs remained significantly above baseline controls, suggesting residual TGFβ1 activity and/or the presence of other contributing factors.

Figure 10:
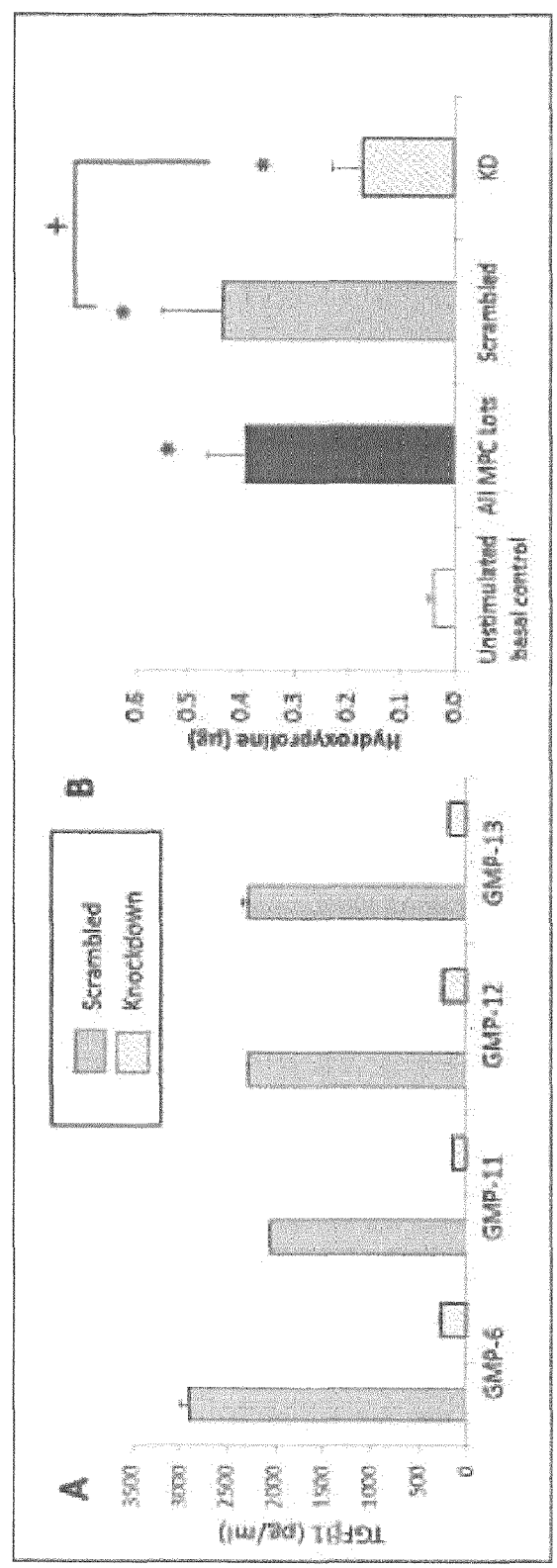
FIG. 10: Effects of TGFβ1 and MPC CM on the matrix composition of fetal human AFCs (lot 4729) in micromass cultures. (A) MPC product from 4 lots were transfected with TGFβ1-targeting siRNA or scrambled negative control. TGFβ1 levels in CM generated from transfected cells are shown. (B) Mean collagen production by fetal AFCs (lot 4729) in response to CM derived from unmanipulated or siRNA transfected MPCs. Data demonstrate significant inhibition of CM bioactivity with TGFβ1 siRNA. Data are expressed as Mean±SD. n=18 normal CM (3-8 replicates/CM) and 4 scrambled or TGFβ1 siRNA transfected MPCs (3 replicates/condition). Significance assigned to p≤0.05 relative to unstimulated basal control (*) or to scrambled control (+).

In summary, the data shows that knockdown MPCs secreted an average of 204.81±52.07 pg/ml TGFβ1, which resulted in production of 0.17±0.06 μg hydroxyproline in AFCs (FIG. 10 and Table 5). This level of hydroxyproline represents the minimum observed effect of MPC CM in the AFC bioassay. The present inventors consider this minimum effect level to define the threshold between sub-potent and potent cells based on currently available data set. In order to increase the stringency of the acceptance criteria for potent cells, the minimum effect level was set 1 SD above the 0.17 μg threshold level to 0.23 μg hydroxyproline.

TABLE 4

CM samples generated from MPC lots tested in fetal AFC
Fetal AFC

| Sample/Lot # | TGFβ1 (pg/ml) | Lot 5945 Average Hydroxyrpoline (μg) | SD | N | Lot 4755 Average Hydroxyrpoline (μg) | SD | N | Lot 4729 Average Hydroxyrpoline (μg) | SD | N | All fAFC Average Hydroxyrpoline (μg) | SD | N |
|---|---|---|---|---|---|---|---|---|---|---|---|---|---|
| GMP-1 | 4189.92 | NT | NT | NT | 0.350 | 0.075 | 3 | NT | NT | NT | 0.350 | 0.075 | 3 |
| GMP-2 | 4202.82 | 0.223 | 0.114 | 2 | 0.433 | 0.150 | 3 | NT | NT | NT | 0.381 | 0.140 | 5 |
| GMP-3 | 2886.46 | NT | NT | NT | 0.292 | 0.048 | 3 | NT | NT | NT | 0.292 | 0.048 | 3 |
| GMP-4 | 3084.53 | 0.386 | 0.126 | 9 | 0.440 | 0.065 | 6 | 0.265 | 0.030 | 8 | 0.358 | 0.117 | 23 |
| GMP-5 | 3191.16 | 0.390 | 0.186 | 10 | 0.359 | 0.064 | 6 | 0.279 | 0.034 | 6 | 0.351 | 0.126 | 22 |
| GMP-6 | 3601.95 | 0.500 | 0.186 | 11 | 0.277 | 0.167 | 6 | 0.297 | 0.217 | 6 | 0.389 | 0.223 | 23 |
| GMP-7 | 2569.11 | 0.300 | 0.097 | 9 | 0.390 | 0.035 | 6 | 0.296 | 0.061 | 6 | 0.325 | 0.063 | 21 |
| GMP-8 | 3178.29 | 0.410 | 0.079 | 6 | 0.409 | 0.073 | 6 | 0.411 | 0.108 | 6 | 0.410 | 0.083 | 18 |
| GMP-9 | 3480.65 | 0.473 | 0.068 | 6 | 0.481 | 0.068 | 6 | 0.390 | 0.109 | 6 | 0.448 | 0.087 | 18 |
| GMP-10 | 4050.11 | 0.237 | 0.095 | 3 | 0.228 | 0.059 | 3 | NT | NT | NT | 0.233 | 0.071 | 6 |
| GMP-11 | 3089.14 | 0.422 | 0.073 | 6 | 0.393 | 0.062 | 6 | 0.414 | 0.114 | 6 | 0.410 | 0.082 | 18 |
| GMP-12 | 3620.38 | 0.479 | 0.099 | 6 | 0.441 | 0.084 | 6 | 0.406 | 0.027 | 6 | 0.442 | 0.078 | 18 |
| GMP-13 | 3537.31 | 0.427 | 0.024 | 6 | 0.483 | 0.074 | 6 | 0.403 | 0.055 | 7 | 0.436 | 0.062 | 19 |
| GMP-14 | 1979.12 | 0.367 | 0.022 | 6 | 0.326 | 0.089 | 6 | 0.329 | 0.081 | 6 | 0.341 | 0.069 | 18 |
| GMP-15 | 3119.66 | 0.434 | 0.134 | 6 | 0.416 | 0.079 | 6 | 0.407 | 0.032 | 6 | 0.419 | 0.087 | 18 |
| GMP-16 | 2963.90 | 0.514 | 0.156 | 6 | 0.463 | 0.036 | 6 | 0.329 | 0.095 | 6 | 0.435 | 0.129 | 18 |
| GMP-17 | 3770.39 | 0.697 | 0.135 | 6 | 0.422 | 0.038 | 6 | 0.420 | 0.120 | 6 | 0.513 | 0.167 | 18 |
| GMP-18 | 2942.00 | 0.524 | 0.118 | 6 | 0.443 | 0.034 | 6 | 0.274 | 0.038 | 6 | 0.414 | 0.128 | 18 |
| All Lot Mean | 3303.16 | 0.426 | | | 0.391 | | | 0.351 | | | 0.386 | | |

TABLE 4-continued

CM samples generated from MPC lots tested in fetal AFC
Fetal AFC

| Sample/Lot # | TGFβ1 (pg/ml) | Lot 5945 Average Hydroxy-rpoline (μg) | SD | N | Lot 4755 Average Hydroxy-rpoline (μg) | SD | N | Lot 4729 Average Hydroxy-rpoline (μg) | SD | N | All fAFC Average Hydroxy-rpoline (μg) | SD | N |
|---|---|---|---|---|---|---|---|---|---|---|---|---|---|
| All Lot SD | 569.56 | 0.106 | | | 0.073 | | | 0.061 | | | 0.065 | | |
| All Lots CV | 0.172 | 0.248 | | | 0.185 | | | 0.173 | | | 0.169 | | |
| Min | 1979.123 | 0.223 | | | 0.228 | | | 0.265 | | | 0.233 | | |
| Max | 4202.824 | 0.697 | | | 0.483 | | | 0.420 | | | 0.513 | | |

NT = not tested
GMP 4-6 Two replicate vials of cells were seeded independently to generate CM. Data represents the average of the replicates.

TABLE 5

CM samples generated from TGFβ1-knockdown MPCs

Fetal AFC-Lot 4729

| Sample/Lot # | Condition | TGF-β1 pg/mL | SD | % Silencing vs Scrambled | Average Hydroxyproline (μg/$10^5$ cells) | SD |
|---|---|---|---|---|---|---|
| Basal medium | | 0 | | | 0.047 | 0.019 |
| All MPC | | 3303.160 | 569.557 | | 0.351 | 0.061 |
| GMP-11 | Scrambled | 2037.455 | 11.39 | — | 0.416 | 0.118 |
| | siTGFβ1 | 143.843 | 4.43 | 92.9 | 0.153 | 0.013 |
| GMP-12 | Scrambled | 2272.886 | 9.71 | — | 0.283 | 0.042 |
| | siTGFβ1 | 236.551 | 3.33 | 89.6 | 0.102 | 0.025 |
| GMP-13 | Scrambled | 2268.294 | 58.23 | — | 0.516 | 0.206 |
| | siTGFβ1 | 180.810 | 0.90 | 92.0 | 0.214 | 0.192 |
| GMP-6 | Scrambled | 2894.451 | 87.15 | — | 0.533 | 0.229 |
| | siTGFβ1 | 258.034 | 15.53 | 91.1 | 0.222 | 0.142 |
| All Scrambled Average | | 2368.272 | 367.60 | — | 0.44 | 0.11 |
| All siTGFb1 Average | | 204.810 | 52.07 | 91.4 | 0.17 | 0.06 |

Establishment of a Preliminary Release Specification for MPCs Based on TGFβ1 Secretion Using the data from our experiments with unmanipulated MPC and TGFβ1 knockdown MPC, the present performed statistical analyses to examine the relationship between TGFβ1 levels and AFC collagen production in vitro and to identify the threshold level of TGFβ1 required for release of MPC clinical product for DDD.

Figure 11:
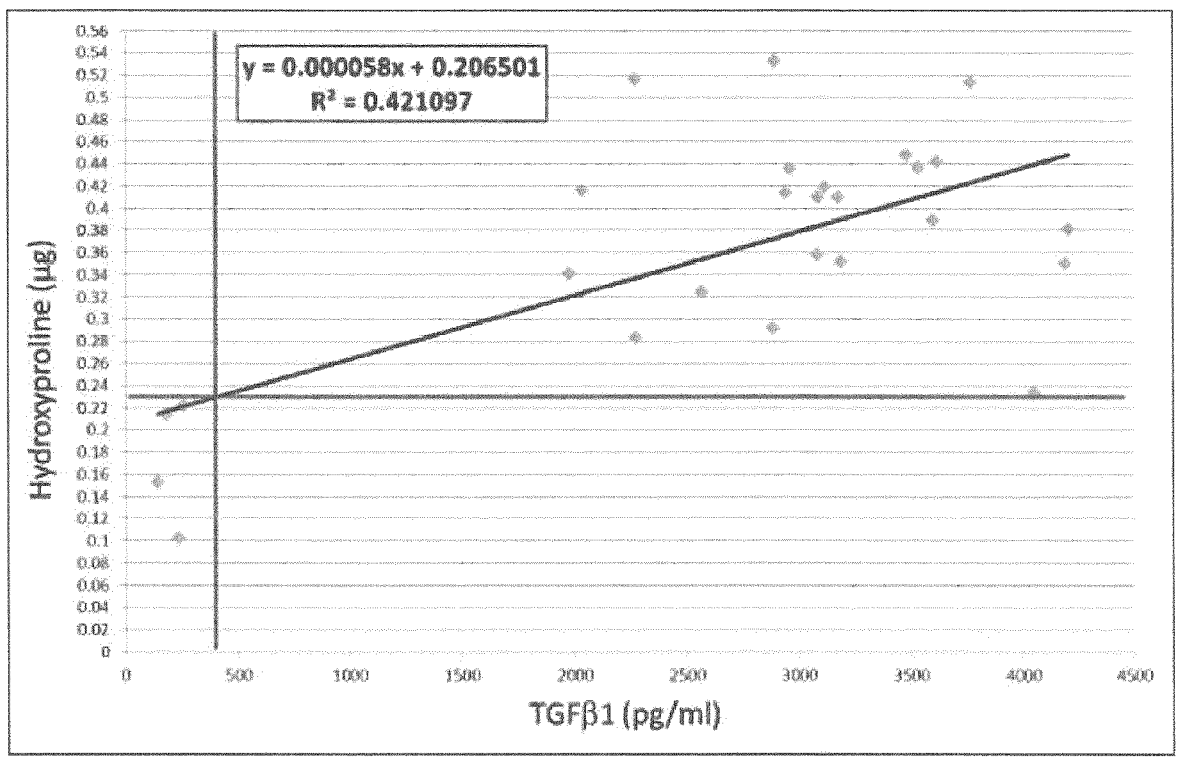
FIG. 11: Regression analysis of TGFβ1 levels in MPC CM vs AFC collagen production.

Relationship Between MPC CM TGFβ1 Levels and Activity in AFC Collagen Synthesis Bioassay It was first determined whether there was a relationship between levels of TGFβ1 present in MPC CM and the effect of MPC CM on collagen production by AFC in vitro. The data from the unmanipulated MPCs and the knockdown MPCs were combined for a total of 26 samples. In this data set, TGFβ1 levels ranged from 143.8-4202.8 pg/ml and collagen levels ranged from 0.10 to 0.53 μg (Table 4 and Table 5). By Pearson's correlation, there was a statistically significant relationship between TGFβ1 levels and collagen production ($r=0.65$, $p \leq 0.001$). Regression analysis was performed to determine the line of best fit between TGFβ1 levels and collagen production ($p \leq 0.001$ see FIG. 11).

Using the minimum effect level of MPC CM in the AFC collagen synthesis bioassay established above, this linear regression model predicts that 405 pg/ml of TGFβ1 is required to stimulate 0.23 μg of collagen production in the AFC bioassay.

Evaluation of Sensitivity and Specificity of the Model

The sensitivity and specificity of the model was examined. Setting the threshold at 405 pg/ml, a contingency analysis was performed. Sensitivity was found to be 100%, i.e. 22/22 of samples predicted to be positive (stimulating ≥0.23 μg hydroxyproline in the AFC bioassay) were in fact truly positive. The present inventors found the specificity to be 100%, i.e. 4/4 of samples predicted to be below the threshold (stimulating <0.23 μg hydroxyproline) were in fact truly negative. There were no false positive samples and there were no false negative samples.

The data presented here support the use of TGFβ1 as a surrogate marker of the potential of MPCs to stimulate collagen production by AFCs in vitro. Using an AFC collagen synthesis bioassay, it was shown that CM samples generated from 18 lots of MPC product stimulate collagen production by AFCs in vitro, and contain robust levels of TGFβ1, as measured by ELISA. This effect was attenuated in CM from TGFβ1-knockdown MPCs, demonstrating a causative role for TGFβ1 in this setting, consistent with previously presented data from neutralizing antibody studies. Combining data from unmanipulated MPCs and TGFβ1 knockdown MPCs, a threshold level of TGFβ1 in MPC CM required for bioactivity in the AFC collagen synthesis bioassay was defined. Statistical analyses of the experimental data led to identification of 405 pg/ml as the minimum level of TGFβ1 required to stimulate a significant increase in collagen production by AFCs in vitro. Therefore, 405 pg/ml TGFβ1 represents the preliminary release specification for MPCs DDD. Together, these data show that ELISA-based detection of TGFβ1 in MPC CM provides a reasonable measure of the potential of MPCs to stimulate endogenous repair processes in the human disc.

Example 5 Optimization of TGFβ1 Potency Assay

The TGFβ1 potency assay measures TGFβ1 levels released by culture-recovered MPC product. There are 2 parts to the assay: (1) Generation of MPC CM from culture-recovered MPC product, and (2) Detection of TGFβ1 levels in CM using a commercially-available enzyme-linked immunosorbent assay (ELISA, R&D Systems Human TGFβ1 Quantikine ELISA).
Assessment of the Impact of Cell Seeding Density, Time in Culture and Inter-Operator Variability on TGFβ1 Levels in MPC CM.

MPC lots 345938 and 2011cc063 were used in this study. MPC products were thawed, washed, counted and seeded in 6-well plates at 25,000 or 50,000 viable cells/cm$^2$ in αMEM supplemented with 10% fetal bovine serum (FBS). The next day, after washing cells with PBS, medium was replaced with CBM+0.5% BSA. CM was collected at 24, 48, 68, 70, 72, 74, 76 and 120 h following CBM medium change. Each time point was collected in triplicate and each CM sample was analyzed for TGFβ1 content in duplicates by ELISA. To determine inter-operator variability, a single vial of each lot of cells was thawed and divided into 2 aliquots, and the experiment, from cell counting to collection of CM, was performed by two operators in parallel.

Figure 12:
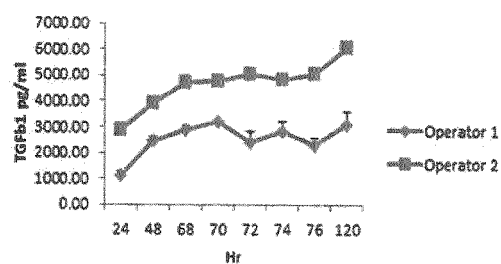
FIG. 12: TGF-β1 secretion by two MPC lots as a function of initial cell seeding density, time and operator. (A) Time course analysis for cells seeded at 25,000 cells/cm$^2$. (B) Time course analysis for cells seeded at 50,000 cells/cm$^2$.
Figure 12:
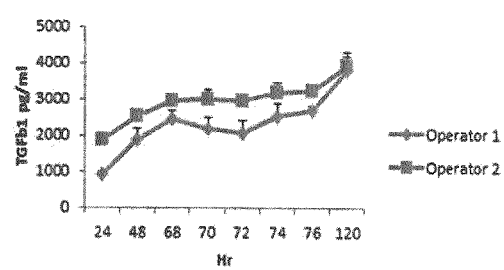
Figure 12:
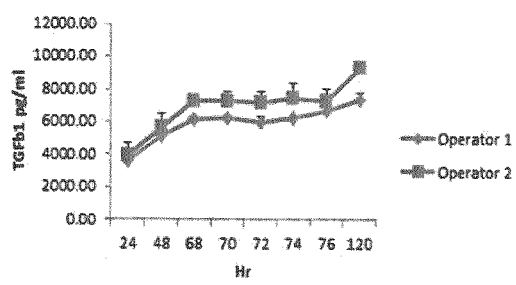
Figure 12:
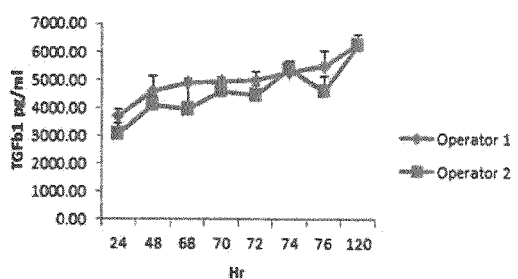

FIG. 12 shows TGFβ1 secretion by two MPC lots as a function of initial cell seeding density, time and operator. FIG. 12A shows data from cells seeded at 25,000 viable cells/cm$^2$. In both lots 345938 and 2011cc063, TGFβ1 levels increased over time (24-120 h), though levels were steady between 68 and 76 h. There was significant inter-analyst variability in TGFβ1 levels determined in CM samples from lot 345938 at each time point examined. Inter-analyst variability of results for lot 2011cc063 was less marked. Data from cells seeded at 50,000 viable cells/cm$^2$ is shown is FIG. 12B. TGFβ1 levels obtained from cells seeded at 50,000 viable cells/cm$^2$ were higher than levels observed when cells were seeded at 25,000 cells/cm$^2$. However, similar to CM samples from cells seeded at the lower density, TGFβ1 levels in CM from cells seeded at 50,000 viable cells/cm$^2$ increased over time, and were steady within the 68-76 h timeframe. Results obtained by each analyst for each lot were comparable when cells were seeded at 50,000 viable cells/cm$^2$.

These data suggest that seeding cells at 50,000 viable cells/cm$^2$ yields more consistent data between analysts compared with seeding cells at 25,000 viable cells/cm$^2$. The data also indicate that TGFβ1 levels are steady between 68 and 76 h, indicating that this timeframe (72±4 h following CBM medium change) represents an acceptable timeframe for CM collection for the TGFβ1 potency assay.
Comparison of 1 N NaOH Vs 1.2 N NaOH/0.5 M HEPES for Neutralization of Acid Activated Samples Prior to assay, CM samples must be acid treated in order to activate latent TGFβ1 to become immunoreactive protein detectable by the TGFβ1 ELISA. This is achieved by addition of 1 N HCl to the samples followed by neutralization to pH 7.2-7.6. The neutralization step can be carried out using 1.2 N NaOH/0.5 M HEPES (according to the TGFβ1 ELISA manufacturer's protocol) or 1 N NaOH. The comparability of unbuffered and buffered NaOH for neutralizing acidified samples for the TGFβ1 ELISA was determined. CM samples from three MPC lots (345938, 2011cc063, 2011cc048) were acid treated. Replicate samples were then neutralized to pH 7.2-7.4 using 1 N NaOH or 1.2 N NaOH/0.5 M HEPES. TGF-31 levels were subsequently determined in duplicate samples by ELISA.

Data are shown in Table 6. TGFβ1 levels were similar in replicate acid activated CM samples neutralized with NaOH and HEPES-buffered NaOH (p>0.05, Student t-test). Therefore, unbuffered NaOH can be substituted for HEPES-buffered NaOH in CM sample preparation for the TGFβ1 potency assay.

TABLE 6

Comparison of TGFβ1 levels in replicate acid-activated CM samples neutralized with 1N NaOH and 1.2N NaOH/0.5M HEPES

| Lot | Neutralization Buffer | Assay Results | | | | | | Corrected TGFβ1 (pg/ml) | | |
|---|---|---|---|---|---|---|---|---|---|---|
| | | Mean OD | SD | CV | TGFβ1 (pg/ml) | Assay SD | Assay CV | Acid Activation Correction | Assay Dilution Correction (x5) | SD |
| 345938 | NaOH | 0.91 | 0.03 | 2.95 | 500.93 | 20.046 | 4 | 701.302 | 3506.51 | 140.32 |
| | NaOH/HEPES | 0.74 | 0.01 | 1.63 | 377.684 | 8.064 | 2.1 | 679.83 | 3399.16 | 72.58 |
| 2011-cc-063 | NaOH | 0.80 | 0.03 | 3.44 | 422.294 | 19.58 | 4.6 | 591.21 | 2956.06 | 137.06 |
| | NaOH/HEPES | 0.66 | 0.03 | 5.21 | 329.076 | 22.763 | 6.9 | 592.34 | 2961.68 | 204.87 |
| 2011-cc-048 | NaOH | 0.69 | 0.04 | 5.23 | 345.448 | 23.532 | 6.8 | 483.63 | 2418.14 | 164.72 |
| | NaOH/HEPES | 0.57 | 0.04 | 6.29 | 270.987 | 22.411 | 8.3 | 487.78 | 2438.883 | 201.70 |

Summary

Two independent operators tested two different initial cell densities (25,000 viable cells/cm$^2$ and 50,000 viable cells/cm$^2$) for secretion of TGFβ1 as a function of time. Results indicate that when cells are seeded at 50,000 viable cells/cm$^2$ there is more consistency between values obtained from two operators than when cells are seeded at a lower density. Importantly, there is little variability in TGFβ1 levels across samples collected between 68 h and 76 h. Based on these data, it is recommended that MPC CM should be prepared by seeding cells at 50,000 viable cells/cm$^2$ and that collection of MPC CM for the TGFβ1 potency assay should be performed at 72±4 h after addition of CBM+0.5% BSA.

The data show that TGFβ1 levels acid-activated CM samples neutralized with 1N NaOH are comparable to samples neutralized with 1.2N NaOH/0.5M HEPES. Therefore, 1 N NaOH is an acceptable substitute for 1.2 N NaOH/0.5 M HEPES for sample neutralization for the TGFβ1 ELISA.

Example 6: Performance of TGFβ1 Potency Assay

Performance of the TGFβ1 ELISA was evaluated by assessment of the following parameters:
1. Assay linearity: standard curves were prepared in calibrator diluent or CBM+0.5% BSA;
2. Matrix interference: rhTGFβ1 was diluted in calibrator diluent or CBM+0.5% BSA; and
3 Assay accuracy and sample linearity: experiments were conducted to examine spike and recovery and TGFβ1 in serially-diluted CM samples.

Assay Linearity

Figure 13:
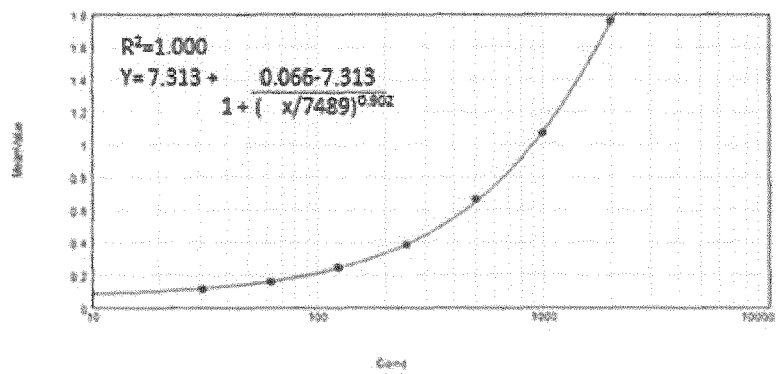
FIG. 13. Linearity of TGFβ1 standard curves using standards from 3 lots of ELISA kits. (A) Standard curves prepared in calibrator diluent. (B) Standard curves prepared in CBM+0.5% BSA.
Figure 13:
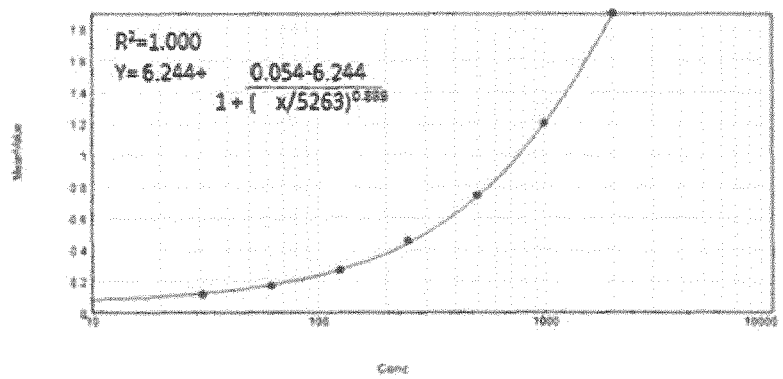
Figure 13:
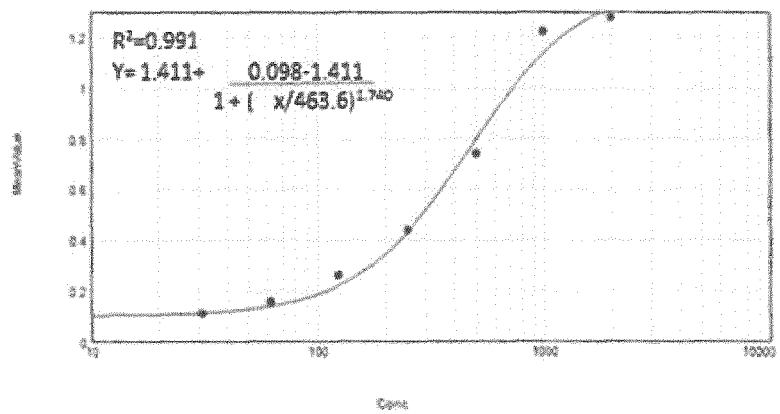
Figure 13:
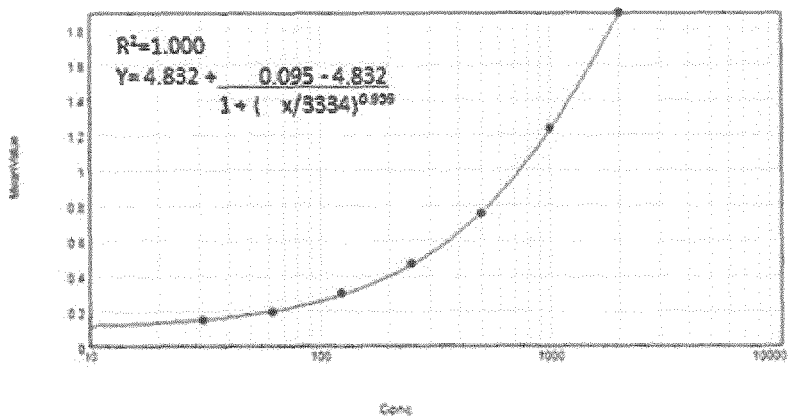
Figure 13:
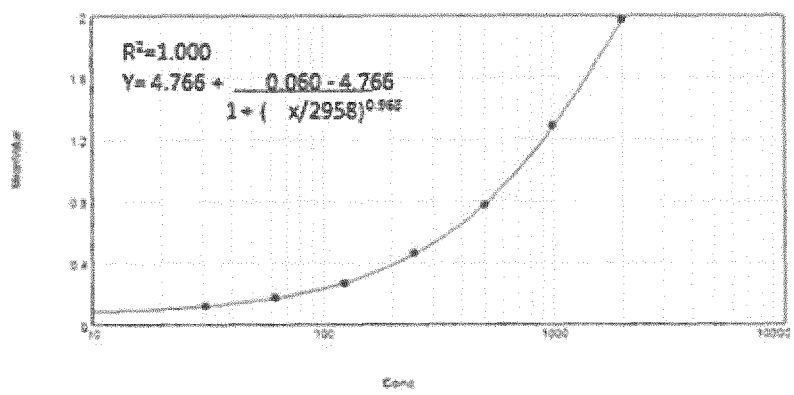
Figure 13:
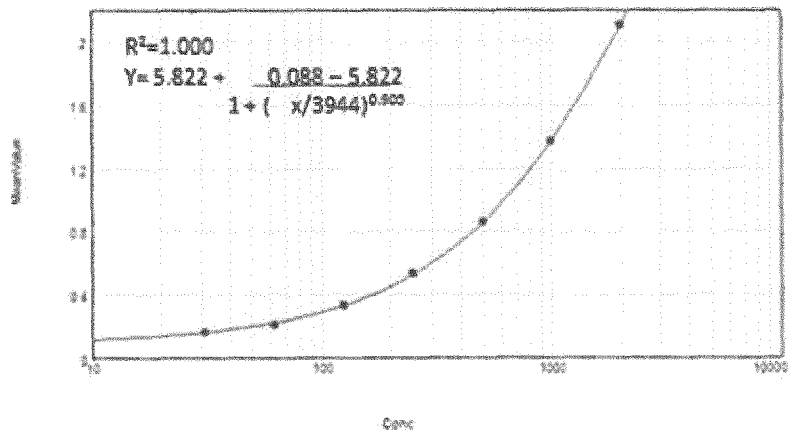

The goodness of fit of the standard curve was assessed. TGFβ1 standards from three separate kits were reconstituted and diluted in calibrator diluent provided in the ELISA kit or CBM+0.5% BSA. Serial dilutions were prepared from 2000 pg/ml. The standard curve established by the kit manufacturer consists of 7 points and a zero point. Therefore, the established range of the standard curve was 31.2 to 2,000 pg/mL. Each standard concentration was analyzed in duplicate. The correlation coefficient ($R^2$) was determined using a 4-parameter logistic nonlinear regression curve fit. Typically, acceptable standard curve $R^2$ is ≥0.95. The correlation coefficients for the three standard curves generated using calibrator diluent ranged from 0.991 to 1.000, while $R^2$=1.000 for all three standard curves prepared in CBM+0.5% BSA. The standard curves are shown in FIG. 13. To ensure the accuracy of the standard curve, TGFβ1 concentrations were back-calculated and % recovery was determined. Overall, % recovery was found to be within 80%-120% (Table 7).

TABLE 7

Standard curves prepared in calibrator diluent and CBM + 0.5 BSA

| | | Calibrator Diluent | | | | | CBM + 0.5% BSA | | | |
| --- | --- | --- | --- | --- | --- | --- | --- | --- | --- | --- |
| Standard Curve | Sample | TGFβ1 (pg/ml) | Mean OD | Back Calc (pg/ml) | % Recovery | Standard Curve | Sample | TGFβ1 (pg/ml) | Mean OD | Back Calc (pg/ml) | % Recovery |
| 1 | 1 | 0 | 0.064 | UND | — | 4 | 1 | 0 | 0.098 | 1.75 | — |
| | 2 | 31.2 | 0.107 | 25.51 | 81.8 | | 2 | 31.2 | 0.144 | 28.66 | 91.8 |
| | 3 | 62.5 | 0.154 | 77.50 | 124.0 | | 3 | 62.5 | 0.192 | 58.96 | 94.3 |
| | 4 | 125 | 0.257 | 148.16 | 118.5 | | 4 | 125 | 0.296 | 129.35 | 103.4 |
| | 5 | 250 | 0.435 | 251.40 | 100.6 | | 5 | 250 | 0.463 | 252.87 | 101.1 |
| | 6 | 500 | 0.738 | 450.59 | 90.1 | | 6 | 500 | 0.751 | 495.61 | 99.1 |
| | 7 | 1000 | 1.22 | 1287.23 | 128.7 | | 7 | 1000 | 1.232 | 1002.61 | 100.3 |
| | 8 | 2000 | 1.274 | 1604.11 | 80.2 | | 8 | 2000 | 1.894 | 2000.89 | 100.0 |
| 2 | 1 | 0 | 0.061 | 2.76 | — | 5 | 1 | 0 | 0.06 | 2.44 | — |
| | 2 | 31.2 | 0.112 | 27.64 | 88.6 | | 2 | 31.2 | 0.115 | 30.51 | 91.8 |
| | 3 | 62.5 | 0.167 | 59.62 | 95.4 | | 3 | 62.5 | 0.171 | 63.29 | 94.3 |
| | 4 | 125 | 0.264 | 121.41 | 97.1 | | 4 | 125 | 0.267 | 123.00 | 103.4 |
| | 5 | 250 | 0.45 | 257.27 | 102.9 | | 5 | 250 | 0.46 | 254.13 | 101.1 |
| | 6 | 500 | 0.739 | 504.99 | 101.0 | | 6 | 500 | 0.77 | 495.98 | 99.1 |
| | 7 | 1000 | 1.198 | 991.14 | 99.1 | | 7 | 1000 | 1.282 | 1002.14 | 100.3 |
| | 8 | 2000 | 1.896 | 2003.48 | 100.2 | | 8 | 2000 | 1.972 | 1999.43 | 100.0 |
| 3 | 1 | 0 | 0.073 | 3.15 | — | 6 | 1 | 0 | 0.095 | 2.54 | — |
| | 2 | 31.2 | 0.113 | 28.17 | 90.3 | | 2 | 31.2 | 0.156 | 29.86 | 95.7 |
| | 3 | 62.5 | 0.156 | 58.36 | 93.4 | | 3 | 62.5 | 0.209 | 56.67 | 90.7 |
| | 4 | 125 | 0.245 | 126.89 | 101.5 | | 4 | 125 | 0.328 | 123.84 | 99.1 |
| | 5 | 250 | 0.381 | 243.15 | 97.3 | | 5 | 250 | 0.533 | 255.98 | 102.4 |
| | 6 | 500 | 0.664 | 518.61 | 103.7 | | 6 | 500 | 0.86 | 504.50 | 100.9 |
| | 7 | 1000 | 1.069 | 986.15 | 98.6 | | 7 | 1000 | 1.365 | 991.46 | 99.1 |
| | 8 | 2000 | 1.758 | 2004.12 | 100.2 | | 8 | 2000 | 2.103 | 2005.11 | 100.3 |

Matrix Interference

To examine matrix interference, rhTGF-β1 (R&D Systems) was prepared in calibrator diluent or in CBM+0.5% BSA at 0, 50, 250 and 1,500 pg/mL. Each concentration was prepared in duplicate. TGFβ1 concentration in each sample was determined by ELISA. Mean concentration and % recovery for each sample are presented in Table 8. In calibrator diluent, the % recovery ranged from 70.4 to 74.7% while in CBM+0.5% BSA recovery ranged from 94.5 to 106.1%.

TABLE 8

Analysis of matrix interference

| Diluent | rhTGFβ1 pg/ml | Repeat | OD | Mean OD | TGFβ1 (pg/ml) | Assay SD | Assay CV | % Recovery |
|---|---|---|---|---|---|---|---|---|
| Calibrator diluent | 0 | 1 | 0.071 | 0.072 | 2.56 | 0.59 | 23.2 | |
| | | 2 | 0.072 | | | | | |
| | 50 | 1 | 0.124 | 0.124 | 35.52 | 0.20 | 0.5 | 71.0 |
| | | 2 | 0.124 | | | | | |
| | 250 | 1 | 0.292 | 0.304 | 176.02 | 13.97 | 7.9 | 70.4 |
| | | 2 | 0.316 | | | | | |
| | 1500 | 1 | 1.167 | 1.174 | 1120.94 | 12.09 | 1.1 | 74.7 |
| | | 2 | 1.18 | | | | | |
| CBM | 0 | 1 | 0.093 | 0.093 | 15.01 | 0.44 | 3 | |
| | | 2 | 0.092 | | | | | |
| | 50 | 1 | 0.148 | 0.149 | 53.06 | 0.87 | 1.6 | 106.1 |
| | | 2 | 0.15 | | | | | |
| | 250 | 1 | 0.362 | 0.374 | 236.14 | 14.48 | 6.1 | 94.5 |
| | | 2 | 0.385 | | | | | |
| | 1500 | 1 | 1.38 | 1.422 | 1468.85 | 86.83 | 5.9 | 97.9 |
| | | 2 | 1.463 | | | | | |

Figure 14:
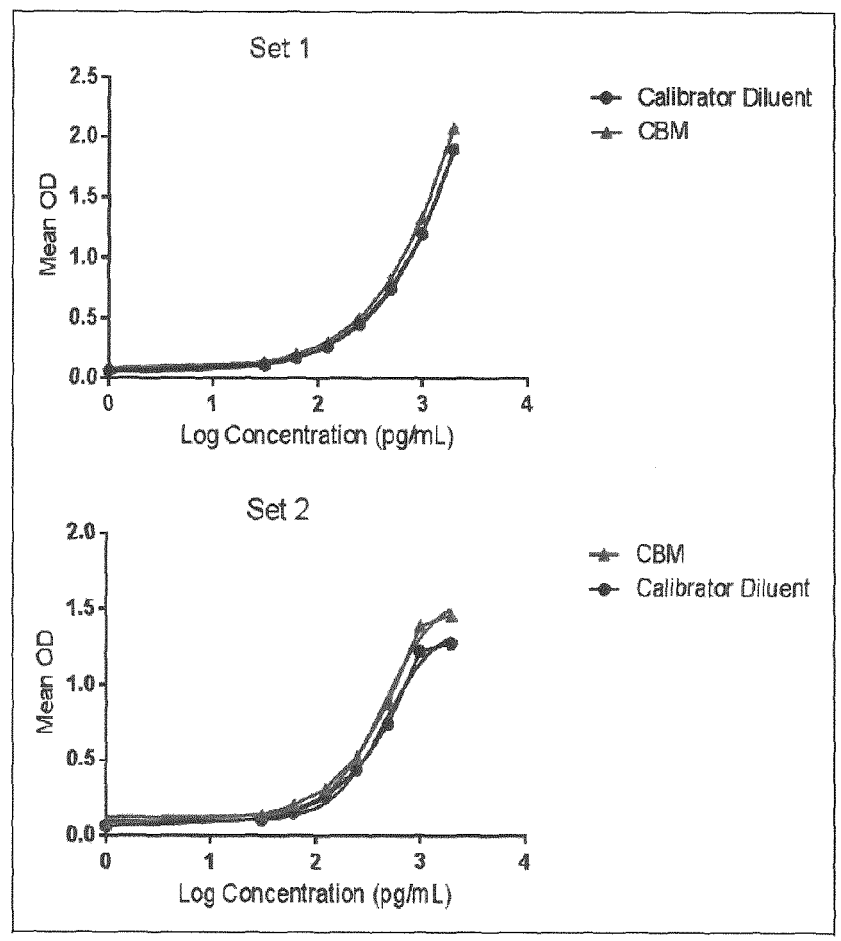
FIG. 14. Comparison of standard curves for TGFβ1 ELISA assay prepared in calibrator diluent and Chondrogenic Basal Medium (CBM)+0.5% BSA, Matrix effect was evaluated by comparing standard curves prepared in calibrator diluent and CBM+0.5% BSA (analyzed in parallel on the same plates). Each standard was represented in duplicate and two independent experiments were performed. ODs were slightly higher when standards were prepared in CBM compared with calibrator diluent, indicating the presence of a matrix effect.

Additionally, matrix effect was evaluated by comparing standard curves prepared in calibrator diluent and CBM+0.5% BSA (analyzed in parallel on the same plates). Each standard was represented in duplicate and two independent experiments were performed. FIG. 14 shows that mean ODs were slightly higher when standards were prepared in CBM compared with calibrator diluent, indicating the presence of a matrix effect.

Assay Accuracy

Spike and recovery experiments were performed to evaluate assay accuracy. Three different concentrations of rhTGFβ1 (50, 250 and 500 pg/mL) were spiked into CM derived from 3 MPC lots (345938, 2011cc063, 2011cc048). Each condition was assayed in duplicate. The percent recovery of TGFβ1 at each concentration was calculated using the following formula:

[Mean measured concentration/Expected concentration]×100

The mean measured concentration corresponds to the TGFβ1 concentration in the spiked sample as determined from the standard curve. The results from the three sets of data are shown in Table 9. Acceptable spike recovery typically ranges from 80-120%. The percent recovery values for all samples ranged from 96.17% to 126.87%. Average TGFβ1 recovery at each concentration tested was calculated: 50 pg/ml: 112.1%, 250 pg/ml: 103.8%, 500 pg/ml: 97.8%.

TABLE 9

Assessment of ELISA accuracy.

| | Spiked | Assay Results | | | |
|---|---|---|---|---|---|
| Lot | rhTGFβ1 (pg/ml) | TβPβ1 (pg/ml) | SD | CV | % Recovery |
| 345938 | 0 | 685.98 | 28.50 | 4.2 | |
| | 50 | 736.78 | 23.66 | 3.2 | 100.1 |
| | 250 | 940.32 | 63.74 | 6.8 | 100.5 |
| | 500 | 1166.31 | 126.60 | 10.9 | 98.3 |
| 2011-cc-063 | 0 | 319.39 | 24.41 | 7.6 | |
| | 50 | 468.64 | 13.41 | 2.9 | 126.9 |
| | 250 | 617.35 | 44.09 | 7.1 | 108.4 |
| | 500 | 809.00 | 9.67 | 1.2 | 98.7 |
| 2011-cc-048 | 0 | 450.99 | 13.96 | 3.1 | |
| | 50 | 547.61 | 5.61 | 1.0 | 109.3 |
| | 250 | 718.54 | 47.51 | 6.6 | 102.5 |
| | 500 | 914.52 | 69.52 | 7.6 | 96.2 |

Sample Linearity

Sample linearity was assessed by assaying CM samples derived from three different MPC lots (22-12-002US, 1857469, 345938) neat and diluted 2×, 5× and 10×. Each sample was evaluated in duplicate. Accuracy (% drift) at each dilution of a given sample was calculated as:

% Drift=(Result−average result of all dilutions)/average result of all dilutions×100

Results are summarized in Table 10. The % drift ranged from −17.8 to 10.5%. Acceptable % drift is typically ±20%.

TABLE 10

Assessment of sample linearity.

| | | | | | Assay Results | | | | Corrected Results | | | Dilution | |
|---|---|---|---|---|---|---|---|---|---|---|---|---|---|
| Lot | Dilution | Repeat | OD | Mean OD | TGF-β1 (pg/mL) | SD | % CV | TGF-β1 (pg/mL) | SD | % CV | Average result | % Drift |
| 22-12002US | 1 | 1 | 2.227 | 2.20 | 2221.94 | 43.04 | 1.9 | 3110.72 | 60.25 | 1.94 | 3784.72 | −17.81 |
| | | 2 | 2.171 | | | | | | | | | |
| | ½ | 1 | 1.402 | 1.39 | 1345.79 | 13.45 | 1 | 3768.22 | 26.90 | 0.71 | | 1.00 |
| | | 2 | 1.384 | | | | | | | | | |
| | ⅕ | 1 | 0.705 | 0.70 | 597.51 | 1.61 | 0.3 | 4182.56 | 8.07 | 0.19 | | 10.51 |
| | | 2 | 0.703 | | | | | | | | | |
| | 1/10 | 1 | 0.443 | 0.42 | 291.24 | 30.97 | 10.6 | 4077.36 | 309.71 | 7.60 | | 7.73 |
| | | 2 | 0.402 | | | | | | | | | |
| 1857469 | 1 | 1 | 1.653 | 1.65 | 1627.88 | 1.23 | 0.1 | 2279.03 | 1.72 | 0.08 | 2443.76 | −6.74 |
| | | 2 | 1.652 | | | | | | | | | |
| | ½ | 1 | 1.036 | 1.02 | 937.91 | 27.74 | 3 | 2626.13 | 55.49 | 2.11 | | 7.46 |
| | | 2 | 0.999 | | | | | | | | | |
| | ⅕ | 1 | 0.485 | 0.50 | 370.80 | 15.60 | 4.2 | 2595.57 | 78.01 | 3.01 | | 6.21 |
| | | 2 | 0.506 | | | | | | | | | |
| | 1/10 | 1 | 0.311 | 0.30 | 162.45 | 10.22 | 6.3 | 2274.30 | 102.21 | 4.49 | | −6.93 |
| | | 2 | 0.297 | | | | | | | | | |
| 345938 | 1 | 1 | 2.122 | 2.11 | 2121.79 | 23.59 | 1.1 | 2970.51 | 33.03 | 1.11 | 3506.29 | −15.28 |
| | | 2 | 2.091 | | | | | | | | | |
| | ½ | 1 | 1.343 | 1.33 | 1278.79 | 18.75 | 1.5 | 3580.61 | 37.50 | 1.05 | | 2.12 |
| | | 2 | 1.319 | | | | | | | | | |
| | ⅕ | 1 | 0.656 | 0.66 | 547.52 | 3.92 | 0.7 | 3832.61 | 19.60 | 0.51 | | 9.31 |
| | | 2 | 0.661 | | | | | | | | | |
| | 1/10 | 1 | 0.393 | 0.39 | 260.10 | 0.77 | 0.3 | 3641.43 | 7.69 | 0.21 | | 3.85 |
| | | 2 | 0.394 | | | | | | | | | |

Summary

The data provide support for the suitability of the TGFβ1 ELISA for measuring TGFβ1 in CM collected from MPC cultures. The $R^2$ value of the standard curve ranged from 0.991-1.000 and TGFβ1 recovery at each standard concentration was found to be within 80-120%. Experiments performed to examine matrix effect indicated higher recovery of TGFβ1 in CBM+0.5% BSA compared to calibrator diluent, and a slight upward and rightward shift in the standard curved prepared in CBM+0.5% BSA compared to calibrator diluent. Therefore, it is recommended that the standard curve be prepared in CBM+0.5% BSA.

BIBLIOGRAPHY

Adams, M. A., & Roughley, P. J. (2006). *Spine*, 31, 2151-2161.
Ausubel, F. M. (Ed.). (1987 including all updates untill present). *Current Protocols in Molecular Biology*. New York: John Wiley & Sons.
Bae, W. C., & Masuda, K. (2011). *The Orthopedic Clinics of North America*, 2011, 585-601, ix.
Bjornsson, S. (1993). *Analytical Biochemistry*, 210, 282-291.
Brown, T. A. (Ed.). (1991). *Essential Molecular Biology: A Practical Approach* (Vol. 1 and 2). Oxford: IRL Press at Oxford University Press.
Buchschacher, G. L., & Panganiban, A. T. (1992). *Journal of Virology*, 2731-2739.
Burns, J. C., Friedmann, T., Driever, W., Burrascano, M., & Yee, J. K. (1993). *Proceedings of the National Academy of Sciences USA*, 8033-8037.
Carter, B. J. (1992). *Current Opinion in Biotechnology*, 533-539.
Cheung, K. M., Karppinen, J., Chan, D., Ho, D. W., Song, Y. Q., Sham, P., et al. (2009). *Spine*, 34, 934-940.
Cima, L. G., Ingber, D. E., Vacanti, J. P., & Langer, R. (1991). *Biotechnology Bioengineering*, 38, 145-158.
Coligan, J. E., Kruisbeek, A. M., Margulies, D. H., Shevach, E. M., & Strober, W. (Eds.). (1991 including all updates until present). *Current Protocols in Immunology*. New York: John Wiley & Sons.
Crock, H. V., & Goldwasser, M. (1984). *Spine*, 9, 702-706.
Fisher-Hoch, S. P., McCormick, J. B., Auperin, D., Brown, B. G., Castor, M., Perez, G., et al. (1989). *Proceedings of the National Academy of Sciences USA*, 56, 317-321.
Freemont, A. J. (2009). *Rheumatology*, 48, 5-10.
Glover, M., & Hames, B. D. (Eds.). (1995 and 1996). *DNA Cloning: A Practical Approach* (Vols. 1-4).
Gronthos, S. (2003). *Journal of Cell Science*, 116(Pt 9), 1827-1835.
Gronthos, S., & Simmons, P. J. (1995). *Blood*, 85(4), 929-940.
Gruber, H. E., Ingram, J. A., Davis, D. E., & Hanley, E. N. (2009). *The Spine Journal: Official journal of the American Spine Society*, 9, 210-215.
Gruber, H. E., Hoelscher, G. L., & Hanley, E. N. (2010). *The Spine Journal: Official journal of the North American Spine Society*, 10, 721-727.
Guerin, H. L., & Elliott, D. M. (2007). *Journal of Orthopaedic Research—Official publication of the Orthopaedic Research Society*, 25, 508-516.
Harlow, E., & Lane, D. (1988). *Antibodies: A Laboratory Manual*. New York: Cold Spring Harbor Laboratory Press.
Hilton, R. C., & Ball, J. (1984). *Annals of the Rheumatic Diseases*, 43, 302-307.
Humzah, M. D., & Soames, R. W. (1988). *The Anatomical Record*, 220, 337-356.
Johann, S. V., Gibbons, J. J., & O'Hara, B. (1992). *Journal of Virology*, 65, 1635-1640.

Johnson, W. E., & Roberts, S. (2007). *Biochemical Society Transactions*, 35, 680-682.

Johnson, W. E., Caterson, B., Eisenstein, S. M., Hynds, D. L., Show, D. M., & Roberts, S. (2002). *Arthritis and Rheumatism*, 46, 2658-2664.

Johnstone, B., Hering, T. M., Caplan, A. I., Goldberg, V. M., & Yoo, J. U. (1998). *Experimental Cell Research*, 238, 265-272.

Kotin, R. M. (1994). *Human Gene Therapy*, 793-801.

Le Maitre, C. L., Freemont, A. J., & Hoyland, J. A. (2005). *Arthritis Research and Therapy*, 7, R732-745.

Le Maitre, C. L., Hoyland, J. A., & Freemont, A. J. (2007). *Arthritis Research and Therapy*, 9, R77.

Le Maitre, C. L., Hoyland, J. A., & Freemont, A. J. (2007). *Arthristis Research and Therapy*, 9, R83.

Le Maitre, C. L., Pockert, A., Buttle, D. J., Freemont, A. J., & Hoyland, J. A. (2007). *Biochemical Society Transactions*, 2007, 652-655.

Lebkowski, J. S., McNally, M. M., Okarma, T. B., & Lerch, L. B. (1988). *Molecular and Cellular Biology*, 3988-3996.

Loreto, C., Musumeci, G., Castorina, A., Loreto, C., & Martinez, G. (2011). *Annals of Anatomy=Anatomischer Anzeiger: Official organ of the Anatomische Gesellschaft*, 193, 156-162.

Marchand, F., & Ahmed, A. M. (1990). *Spine*, 15, 402-410.

Masuda, K. (2008). European Spinel Journal: *Official publication of the European Spine Society, the European Spinal Deformity Society, and the European Section of the Cervical Spine Research Society*, 17 Suppl 4, 441-451.

Melrose, J., Ghosh, P., Taylor, T., Latham, J., & Moore, R. (1997). *Journal of Spinal Disorders*, 10(1), 56-67.

Melrose, J., Roberts, S., Smith, S., Menage, J., & Ghosh, P. (2002). *Spine*, 27, 1278-1285.

Melrose, J., Smith, S., Ghosh, P., & Taylor, T. (2001). *Cells Tissues Organs*, 168, 137-146.

Miller, A. D. (1990). *Human Gene Therapy*, 7, 5-14.

Miller, A. D., & Rosman, G. J. (1989). *Biotechniques*, 7, 980-990.

Miller, A. D., Garcia, J. V., von Suhr, N., Lynch, C. M., Wilson, C., & Eiden, M. V. (1991). *Journal of Virology*, 65, 2220-2224.

Murata, Y., Onda, A., Rydevik, B., Takahashi, I., & Olmarker, K. (2006). *Spine*, 31, 530-535.

Muzyczka, N. (1992). *Current Topics in Microbiology and Immunology*, 158, 97-129.

O'Halloran, D. M., & Pandit, A. S. (2007). *Tissue Engineering*, 13, 1927-1954.

Perbal, B. V. (1984). *A Practical Guide to Molecular Cloning*. New York: Wiley.

Purmessur, D., Walter, B. A., Roughley, P. J., Laudier, D. M., Hecht, A. C., & Iatridis, J. A. (2013). *Biochemical and Biophysical Research Communications*, 433, 151-156.

Raj, P. P. (2008). *Pain Practice*, 8, 18-44.

Risbud, M. V., & Shapiro, I. M. (2014). *Nature Reviews. Rheumatology*, 10, 44-56.

Roberts, S., Eisenstein, S. M., Menage, J., Evans, E. H., & Ashton, I. K. (1995). *Spine*, 20, 2645-2651.

Roberts, S., Evans, H., Trivedi, J., & Menage, J. (2006). *The Journal of Bone and Joint Surgery. American Volume*, 88 Suppl 2, 10-14.

Sambrook, J., & Green, M. R. (2012). *Molecular Cloning: A Laboratory Manual (Fourth Edition)*. New York: Cold Spring Harbour Laboratory Press.

Scarpa, M., Cournoyer, D., Munzy, D. M., Moore, K. A., Belmont, J. W., & Caskey, C. T. (1991). *Virology*, 75, 849-852.

Schmidt, H., Kettler, A., Heuer, F., Simon, U., Claes, L., & Wilke, H. J. (2007). *Spine*, 32, 748-755.

See, F., Seki, T., Psaltis, P. J., Sondermeijer, H. P., Gronthos, S., Zannettino, A. C., et al. (2011). *Journal of Cellular and Molecular Medicine*, 15, 2117-2129.

Seguin, C. A., Pilliar, R. M., Roughley, P. J., & Kandel, R. A. (2005). *Spine*, 30, 1940-1948.

Shamji, M. F., Setton, L. A., Jarvis, W., So, S., Chen, J., Jing, L., et al. (2010). *Arthritis and Rheumatism*, 62, 1974-1982.

Shelling, A. N., & Smith, M. G. (1994). *Gene Therapy*, 7, 165-169.

Shen, B., Melrose, J., Ghosh, P., & Taylor, T. (2003). *European Spine Journal*, 12, 66-75.

Sommerfelt, M. A., & Weiss, R. A. (1990). *Virology*, 76, 58-59.

Urban, J. P., Smith, S., & Fairbank, J. C. (2004). *Spine*, 29, 2700-2709.

Vacanti, C. A., Langer, R., Schloo, B., & Vacanti, J. P. (1991). *Plastic Reconstructive Surgery*, 88, 753-749.

Vacanti, J. P., Morse, M. A., & Saltzman, W. M. (1988). *Journal of Pediatric Surgery*, 23, 3-9.

Vincent, K. A., Moore, G. K., & Haigwood, N. L. (1990). *Vaccine*, 353-359.

Wadstrom, J., & Tengblad, A. (1993). *Journal of Medical Science*, 98, 159-167.

Wang, J., Markova, D., Anderson, D. G., Zheng, Z., Shapiro, I. M., & Risbud, M. V. (2011). *The Journal of Biologoical Chemistry*, 286, 39738-39749.

Watanabe, H., Yamada, Y., & Kimata, K. (1998). *Journal of Biochemistry*, 124, 687-693.

Weigel, P. H., Fuller, G. M., & Le Boeuf, R. D. (1986). *Journal of Theoretical Biology*, 119, 219-234.

Wilson, C., Reitz, M. S., Okayama, H., & Eiden, M. V. (1989). *Journal of Virology*, 63, 2374-2378.

Zannettino, A. C., Buhring, H. J., Niutta, S., Watt, S. M., Benton, M. A., & Simmons, P. J. (1998). *Blood*, 92(8), 2613-2628.

Zhou, S. Z., Cooper, S., Kang, L. Y., Ruggieri, L., Heimfeld, S., Srivastava, A., et al. (1994). *The Journal of Experimental Medicine*, 179, 1867-1875.

The invention claimed is:

1. A method for determining if human mesenchymal lineage precursor or stem cells in a population of cells are sufficiently potent for use in treating a degenerative disc disease, the method comprising:
 (i) culturing a population of cells comprising human mesenchymal lineage precursor cells or stem cells in a culture medium for a suitable culture time period;
 (ii) determining at the end of the culture period the amount of TGFβ1 released by the cultured population of cells into the culture medium; and
 (iii) determining that the human mesenchymal lineage precursor or stem cells in the population are sufficiently potent for such use if the [determined] amount of TGFβ1 determined in step (ii) is at least 2800 pg/$10^6$ cells present at the end of the culture period.

2. The method of claim 1, wherein the population of step (i) is a population enriched for mesenchymal lineage precursor or stem cells.

3. The method of claim 1, wherein the method comprises seeding the cells in a culture vessel at a density of about 50,000 viable cells/$cm^2$.

4. The method of claim 1, wherein the method comprises culturing the cells in chondrogenic basal medium supplemented with 0.5% bovine serum albumin.

5. The method of claim 1, wherein the culture period is at least 68 [to 76] hours.

6. The method of claim 1, wherein the method comprises collecting a sample of the culture medium in which the cells were cultured.

7. The method of claim 6, wherein the method comprises activating latent TGFβ1 in the culture medium prior to determining the amount of TGFβ1 in the culture medium.

8. The method of claim 7, wherein activating latent TGFβ1 comprises adding an acid to the culture medium sample to lower the pH of the culture medium.

9. The method of claim 8, wherein the method comprises concentrating the culture medium sample prior to lowering the pH.

10. The method of claim 8, wherein, following addition of the acid, the culture medium is neutralised to a pH of 7.2 to 7.6.

11. The method of claim 1, wherein the method comprises determining the amount of TGFβ1 in the culture medium by enzyme-linked immunosorbent assay (ELISA).

\* \* \* \* \*